United States Patent
Wessler et al.

(10) Patent No.: US 6,420,117 B1
(45) Date of Patent: Jul. 16, 2002

(54) MINIATURE INVERTED REPEAT TRANSPOSABLE ELEMENTS AND METHODS OF USE

(75) Inventors: Susan R. Wessler, Athens, GA (US); Alexandra M. Casa, Ithaca, NY (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/662,402

(22) Filed: Sep. 14, 2000

Related U.S. Application Data

(60) Provisional application No. 60/153,812, filed on Sep. 14, 1999.

(51) Int. Cl.[7] .......................... C12Q 1/68; C07H 21/02; C07H 21/04; A01H 1/00; A01H 9/100

(52) U.S. Cl. .......................... 435/6; 435/91.1; 435/183; 435/412; 536/23.1; 536/23.5; 536/24.31; 536/24.33; 800/278; 800/295

(58) Field of Search .......................... 435/6, 91.1, 91.2, 435/23.1, 23.5, 24.31, 24.33

(56) References Cited

U.S. PATENT DOCUMENTS

| | | | | |
|---|---|---|---|---|
| 5,874,215 A | | 2/1999 | Kuiper et al. .................. | 435/6 |
| 6,100,030 A | * | 8/2000 | Feazel et al. .................. | 435/6 |

FOREIGN PATENT DOCUMENTS

| | | |
|---|---|---|
| EP | 0 534 858 A1 | 3/1993 |
| EP | 0 721 987 A1 | 7/1996 |
| WO | WO 96/17082 | 6/1996 |
| WO | WO 98/30721 | 7/1998 |

OTHER PUBLICATIONS

Wessler et al. (The Plant Cell (1992) 4:1283–1294, GenEmbl Accession No.: S48688).*

Spell et al. (Mol. Gen Genet (1988) 211: 364–366, GenEmbl Accession No.: X06934).*

Austin et al., "Comparative mapping in $F_{2:3}$ and $F_{6:7}$ generations of quantitative trait loci for grain yield components in maize," *Theoretical and Applied Gentics*, 92:817–826 (1996).

"BLAST," National Institutes of Health [online] United States, [retrieved Feb. 9, 2001]. Retrieved from the Internet: <URL:http://www.ncbi.nlm.nih.gov/gorf/b12.html>, 1 page.

Britten et al., "[29] Analysis of Repeating DNA Sequences by Reassociation," *Methods in Enzymology*, 29:363–418 (1974).

Bureau et al., "Tourist: a Large Family of Small Inverted Repeat Elements Frequently Associated with Maize Genes," *The Plant Cell*, 4(10), 1283–1294 (1992).

Bureau et al., "Stowaway: a New Family of Inverted Repeat Elements Associated with the Genes of Both Monocotyledonous and Dicotyledonous Plants," *The Plant Cell*, 6(6):907–916 (1994).

Bureau et al., "Mobile inverted–repeat elements of the Tourist family are associated with the genes of many cereal grasses," *Proceedings of the National Academy of Sciences, USA*, 91(4):1411–1415 (1994).

Bureau et al., "A computer–based systematic survey reveals the predominance of small inverted–repeat elements in wild–type rice genes," *Proceedings of the National Academy of Sciences*, USA, 93(16):8524–8529 (1996).

Burr et al., "Gene Mapping with Recombinant Inbreds in Maize," *Genetics*, 118(3):519–526 (1988).

Carels et al., "The gene distribution of the maize genome," *Proceedings of the National Academy of Sciences USA*, 92(24):11057–11060 (1995).

Carey et al., "Evolutionary analysis of retrotransposon insertion sites adjacent to specific genes within Zea," Abstract, p. 102, and Poster #118, $41^{st}$ Annual Maize Genetics Conference, Mar. 11–14, Lake Geneva, WI (1999).

Casa et al., "MITEs, a novel class of "smart" molecular marker located preferentially in genic regions," Abstract, p. 103, and Poster #119, $41^{st}$ Annual Maize Genetics Conference, Mar. 11–14, Lake Geneva, WI (1999).

Casa et al., "The MITE family Heartbreaker (Hbr): molecular markers in maize," *Proceedings of the National Academy of Sciences*, USA, 97(18):10083–10089 (Aug. 29, 2000).

Casacuberta et al., "Presence of miniature inverted–repeat transposable elements (MITEs) in the genome of *Arabidopsis thaliana*: characterisation of the Emigrant family of elements," *The Plant Journal*, 16(1):79–85 (1998).

Cresse et al., "Mu1–Related Transposable Elements of Maize Preferentially Insert into Low Copy Number DNA," *Genetics*, 140(1):315–324 (1995).

Don et al., "Touchdown' PCR to circumvent spurious priming during gene amplification," *Nucleic Acids Research*, 19(14):4008 (1991).

Doyle, "Meeting Summary: The Tenth International Genome Sequencing and Analysis Conference, Miami Beach, Florida, Sep. 17–20, 1998," *Microbial and Comparative Genomics*, 3(4):255–257 (1998).

Izsvák et al., "Short Inverted–Repeat Transposable Elements in Teleost Fish and Implications for a Mechanism of Their Amplification," *Journal of Molecular Evolution*, 48(1):13–21 (Jan., 1999).

(List continued on next page.)

Primary Examiner—Kenneth R. Horlick
Assistant Examiner—Alexander H. Spiegler
(74) *Attorney, Agent, or Firm*—Mueting, Raasch & Gebhardt, P.A.

(57) ABSTRACT

The present invention provides methods of using miniature inverted repeat transposable elements, including producing a DNA fingerprint of an individual, detecting at least one polymorphism between the nucleic acid fragments of two individuals, and correlating the presence of an amplified fragment to a phenotype.

39 Claims, 11 Drawing Sheets

OTHER PUBLICATIONS

Lander et al., "MapMaker: An interactive Computer Package for Constructing Primary Genetic Linkage Maps of Experimental and Natural Populations," *Genomics,* 1:174–181 (1987).

Lee et al., "Tools for High Resolution Genetic Mapping in Maize—Status Report," Abstract No. P268, Plant & Animal Genome VII Conference [online]. Town & Country Hotel, San Diego, CA, Jan. 17–21, 1999 [retrieved Sep. 13, 2000]. Retrieved from the Internet: <URL:http://www.intl–pag.org/pag/7/abstracts/pag7605.html>, 1 page.

Liu et al., "Genome– Wide High–Resolution Mapping by Recurrent Intermating Using *Arabidopsis thaliana* as a Model," *Genetics,* 142(1):247–258 (1996).

Maes et al., "Plant tagnology," *Trends in Plant Science,* 4(3):90–96 (Mar., 1999).

"MaizeDB," Maize Genome database, Missouri Maize Project, University of Missouri Maize Genomics Center [online]. University of Missouri, [retrieved Jan. 15, 2001]. Retrieved from the Internet: <URL:http://www.agron.missouri.edu/>, 2 pages.

Mazars et al., "Direct sequencing by thermal asymmetric PCR," *Nucleic Acids Research,* 19(17):4783 (1991).

McCouch et al. "Molecular mapping of rice chromosomes," *Theoretical and Applied Genetics,* 76, 815–829 (1988).

National Center for Biotechnology Information, National Library of Medicine, National Institutes of Health, GenBank Locus ZMDNATBP1, Accession No. X90652, "*Z.mays* DNA for tbpl gene," [online]. Bethesda, MD [retrieved on Jan. 12, 2001]. Retrieved from the Internet:<URL:http://www.ncbi.nlm.nih.gov/query.fcgi?cmd=Retrieve&db=Nucleotide&list_uids=945021&dopt=GenBank>, 4 pages.

National Center for Biotechnology Information, National Library of Medicine, National Institutes for Health, GenBank Locus AF050452, Accession No. AF050452, "*Zea mays* retrotransposon Opie–3 3' LTR, partial sequence," [online]. Bethesda, MD [retrieved on Jan. 12, 2001]. Retrieved from the Internet:<URL:http://www.ncbi.nlm.nih.gov/query.fcgi?cmd=Retrieve&db=Nucleotide&list$_{13}$ uids=3452305&dopt=GenBank>, 2 pages.

National Center for Biotechnology Information, National Library of Medicine, National Institutes of Health, GenBank Locus AF050453, Accession No. AF050453, "*Zea mays* retrotransposon Opie–3 5' LTR, partial sequence," [online]. Bethesda, MD [retrieved on Jan. 12, 2001]. Retrieved from the Internet:<URL:http://www.ncbi.nlm.nih.gov/query-.fcgi?cmd=Retrieve&db=Nucleotide&list_uids=2735839&dopt=GenBank>, 2 pages.

National Center for Biotechnology Information, National Library of Medicine, National Institutes of Health, GenBank Locus AF010283, Accession No. AF010283, "Sorghum bicolor ADP–glucose pyrophosphorylase subunit SH2, transcriptional regulator, NADPH–dependent reductase A1–a and NADPH–dependent reductase A1–b genes, complete cds.," [online]. Bethesda, MD [retrieved on Jan. 12, 2001]. Retrieved from the Internet:<URL:http://www.ncbi.nlm.nih.gov/query.fcgi?cmd=Retrieve&db=Nucleotide&list_uids=2735839&dopt=GenBank>, 14 pages.

Oosumi et al., "Mariner transposons in humans," *Nature,* 378, 672 (1995).

Oosumi et al., "Identification of Putative Nonautonomous Transposable Elements Associated with Several Transposon Families in *Caenorhabditis elegans,*" *Journal of Molecular Evolution,* 43(1):11–18 (1996).

Osborn et al., "Comparison of Flowering Time Genes in *Brassica rapa, B. napus* and *Arabidopsis thaliana,*" *Genetics,* 146(3):1123–1129 (1997).

Pereira et al., "Construction of an RFLP map in sorghum and comparative mapping in maize," *Génome,* 37(2):236–243 (1994).

Sambrook et al, *Molecular Cloning: A Laboratory Manual,* second edition, Cold Spring Harbor Laboratory Press, Cold Spring Harbor, New York, Title page, publication page and table of contents only, 30 pages (1989).

Tatusova et al., "BLAST 2 Sequences, a new tool for comparing protein and nucleotide sequences," *FEMS Microbiology Letters,* 174(2):247–250 (May 15, 1999).

Tautz et al., "Hypervariability of simple sequences as a general source for polymorphic DNA markers," *Nucleic Acids Research,* 17(16):6463–6471 (1989).

Tikhonov et al., "Colinearity and its exceptions in orthologous adh regions of maize and sorghum," *Proceedings of the National Academy of Sciences,* USA, 96(13):7409–7414 (Jun. 22, 1999).

Van den Broeck et al., "Transposon Display identifies individual transposable elements in high copy number lines," *The Plant Journal,* 13(1):121–129 (1998).

Vos et al., "AFLP: a new technique for DNA fingerprinting," *Nucleic Acids Research,* 23(21):4407–4414 (1995).

Wang et al., "Display of Miniature Inverted Repeat Transposable Elements in maize," Abstract, p. 90, and Poster #94, 41$^{st}$ Annual Maize Genetics Conference, Mar. 11–14, Lake Geneva, WI (1999).

Waugh et al., "Genetic distribution of Bare–1–like retrotransposable elements in the barley genome revealed by sequence–specific amplification polymorphisms (S–SAP)," *Molecular and General Genetics,* 253(6):687–694 (1997).

Wessler, "Phenotypic Diversity Mediated by the Maize Transposable Elements Ac and Spm," *Science,* 242(4877):399–405 (1988).

Wessler et al., "LTR–retrotransposons and MITEs: important players in the evolution of plant genomes," *Current Opinions in Genetics & Development,* 5(6):814–821 (1995).

Wessler, "Transposable elements associated with normal plant genes," *Physiologia Plantarum,* 103:581–586 (1998).

Wessler, "MITEs: Transposable Elements that Create Allelic Diversity," Abstract, 10$^{th}$ International Genome Sequencing and Analysis Conference, Sep. 17–20, Miami Beach, FL, p. C–15 (1998).

Wessler et al., "MITEs: Transposable elements that create allelic diversity and serve to anchor a novel class of "smart" molecular markers," Abstract, slides, and Plenary Talk, 41$^{st}$ Annual Maize Genetics Conference, Mar. 11–14, Lake Geneva, WI, p. 19 (Mar. 11, 1999).

Wessler, Susan R., "Tourist and Retro–Elements of Maize," Grant Abstract, Grant No. 5R01GM32528–15 [online]. National Institutes of General Medical Sciences, National Institutes of Health, project dates Jul. 1, 1983–Jan. 31, 2000 [retrieved on Jan. 12, 2001]. Retrieved from the Internet: URL:http.commons.cit.nih.gov/crisp_historical/ crisp_lib-.getdoc?textkey=2654983&p_grant_num=5R01GM32528–15&p_query=ticket=18343&p_audit_session_id=334651&p_keywords=>, 2 pages.

Zhang et al., "Recent, extensive, and preferential insertion of members of the miniature inverted–repeat transposable element family Heartbreaker into genic regions of maize," *Proceedings of the National Academy of Sciences,* USA, 97(3):1160–1165 (Feb. 1, 2000).

Zhao et al., "Characterization and genetic mapping of a short, highly repeated, interspersed DNA sequence from rice (*Oryza sativa* L.)," *Molecular and General Genetics,* 231(3):353–359 (1992).

* cited by examiner (A)
TTAGGGTCTCTGTTTGGTTCAGCTTTTTCTGACCAGCTTTTCTGAAAAATCTGGTTGTGTGGAGAGAATCTGGCTGTCCCAGAATCTGAGTATTATTATGATTACATGTAGA
GGAATATAAAGTTGTTCATAGGGCTCAGAATCTAGAAAGTGACATATTCCTAATATTACAACGACTCAACAGATTATGTGTTTATGTTGATTTTGGATGGTTTTTG
CCCAACGAATTTTATAGAAGCTGGCTGAAAAGCTGAGAGTTTGGCGGTCCGCAGCAGTTTTGGTGGCCAGAAGCTGCCAGAAGCCGAAACAACAGGCCCTTA
(SEQ ID NO:26)

(B)
GGGCTTGTTCGGTTAGGGCTGGATTGAGGGGATTGAGTGATTAAATCCCCTCTATACAAATTTAAATAGGAGGGGATTAATCCCCTCCAATCCCCTCTCAAAC
CCCTTCAAACCGAACAAGCCC
(SEQ ID NO:27)

(C)
GGTCTATTGGTTGAGCTGTGCGTGTGAAAAAGTTTGCTATGGACTGTGAGCTGTGAAAAAATCTGCTGTAAGCTGTTAAAAAGCTAAAAACCGTTTGGT
TGAAACCACTAAGTCGTTAAAAATTCCTTCGATATGTTTCACAGTTACATCCGAAAAAACCACTAAAAGCCAGTCTAGAGGTGCTTTCAGATTTGCACTACGAGA
AAGTCGGCTTTTAGAAAAAGTTGCTTCCTAGATCCAGCCCTTTGGTTGGCTTTTAGGGGTGCAAAACAAGCCAAAAGTCAAACAACAAACACACC
(SEQ ID NO:28)

(D)
CACTTAGGTTCCGTTTGTTTCTTTCATTTTGAGGAATTGGAATCTTACTAATGATTAGGCTAGTTTTTTTAGAATGTAACATTCCACCACTTTCCAAAGTTATCAT
ATAAGCTTATCTCAAATTCATGAGGCGAGAGATGGAAATTGATTCTATAGATTTACATGCACAACTTATAGCACACTCTTCTACTTGCTTCGCT
ATAACATAAATAAATGTAGTATATAATACTATCTCTCATGATTTAGGATAAATATTACAAATATATATTACATATATAAATATACGAATTAATTAGTTTTGTATAAATTATAATT
ATTAAAATGGAATTCAATTCCAACGAAACAAACGGGCCTTAAGT
(SEQ ID NO:29)

*Fig. 3*

MseI+0Tm54.5>

SEQ NO:25    GACGATGAGTCCTGAG TAA>

SEQ NO:23    MseI 5'-GACGATGAGTCCTGAG TAA--------------------------
                  3'-TACTCAGGACTCAT T--------------------------

<HbrInt5-F(SEQ ID NO:30)
                                                    <GTCGAAAAGACTTTTAGACCG

Fig. 4A

SEQ NO:26   1  5'-GGGTCTCTGTTTGGTTCAGCTTTTTTCTGACCAGCTTTTCTGAAAATCTGGC

<HbrInt5-E(SEQ ID NO:24)
            A       <CTTAGACCGACACCCCTCTTAG

51   TGTGGAGAGAATATAAGTTGCTGTGGGAGAATCTGGCTGAGTATTATTATGATTACA

101   TGTAGAGGAATATAAGTTGTTCATAGGGCTCAGAATCTAGAAAGTGACA

151   TATTCCTAATATTACAACGACTCAACAGATTATGTGTTTATGTTGATTTT

201   GGATGGTTTTTGCCCCAACGAATTTTATAGAAGCTGGCTGAAAAGCTGAG

251   AGTTTGGCGGTCCGCAGCAGCTTTTTGGTGGCCTGCCAGAAGCCG

301   AAACAAACAGGCCC-3'

Fig. 4B

SEQUENCE LISTING

```
<160> NUMBER OF SEQ ID NOS: 40

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 1
gggtctgttt ggtt                                                         14

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 2
gggcctgttt gttt                                                         14

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 3
gcagtcagtc cgtcatcctt g                                                 21

<210> SEQ ID NO 4
<211> LENGTH: 20
<212> TYPE: DNA
<213> ORGANISM: Artificial Sequence
<220> FEATURE:
```

```
<223> OTHER INFORMATION: Description of Artificial Sequence:
      Oligonucleotide primer

<400> SEQUENCE: 4
atccttgcct gaaagcagcg                                                    20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 5
gtgcatcaat ctccaaaatc                                                    20

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 6
tcaacgtttc ctagacgg                                                      18

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 7
tccaatacgt aaacagtgc                                                     19

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 8
ctattagcca cttggtgc                                                      18

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 9
tcttttggct ctttgagac                                                     19

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:
```

Oligonucleotide primer

<400> SEQUENCE: 10
cgatcagata ctagggcata c                                              21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:
        Oligonucleotide primer

<400> SEQUENCE: 11
tcatctccgc tttgcgtagc                                                20

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:
        Oligonucleotide primer

<400> SEQUENCE: 12
tgaaacgagg atctaatcct atccg                                          25

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:
        Oligonucleotide primer

<400> SEQUENCE: 13
agcctaaagg gttccttg                                                  18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:
        Oligonucleotide primer

<400> SEQUENCE: 14
tttgaagcca gcatcttg                                                  18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence:
        Oligonucleotide primer

<400> SEQUENCE: 15
ctgtccaccc atcaaatc                                                  18

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:
        Oligonucleotide primer

```
<400> SEQUENCE: 16
tgtgttcttg tctgttccag                                              20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 17
tcctggcatc atcagcttc                                               19

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 18
gccgctctcg tagtagaact tg                                           22

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 19
accgcagcac tttaacacaa g                                            21

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 20
tggaaatgag gatgccgac                                               19

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 21
cgtaccctaa ggctccacaa g                                            21

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide primer
```

```
<400> SEQUENCE: 22
ccgaggttat agtaggaccg taattag                                              27

<210> SEQ ID NO 23
<211> LENGTH: 16
<212> TYPE: DNA
<213> ORGANISM: Artificial Sequence
<220> FEATURE:
<223> OTHER INFORMATION: Description of Artificial Sequence:  Adaptor
      oligonucleotide

<400> SEQUENCE: 23
gacgatgagt cctgag                                                          16

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 24
gattctcccc acagccagat tc                                                   22

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 25
gacgatgagt cctgagtaa                                                       19

<210> SEQ ID NO 26
<211> LENGTH: 319
<212> TYPE: DNA
<213> ORGANISM: Zea mays

<400> SEQUENCE: 26
ttagggtctg tttggttcag cttttttctg accagctttt ctgaaaatct ggttgtggag          60
agaatctggc tgtgggagaa tctgagtatt attatgatta catgtagagg aatataaagt         120
tgttcatagg gctcagaatc tagaaagtga catattccta atattacaac gactcaacag         180
attatgtgtt tatgttgatt ttggatggtt tttgccccaa cgaattttat agaagctggc         240
tgaaaagctg agagtttggc ggtccgcagc agcttttggt ggccagaagc tgccagaagc         300
cgaaacaaac aggcccctta                                                    319

<210> SEQ ID NO 27
<211> LENGTH: 128
<212> TYPE: DNA
<213> ORGANISM: Zea mays

<400> SEQUENCE: 27
gggcttgttc ggttagggct ggattgaggg ggattggagt ggattaaatc cccttctata          60
caaatttaaa taggagggga tttaatcccc tccaatccct ctcaaacccc ttcaaaccga         120
acaagccc                                                                 128

<210> SEQ ID NO 28
```

<211> LENGTH: 316
<212> TYPE: DNA
<213> ORGANISM: Zea mays

<400> SEQUENCE: 28

```
ggtctatttg gttgagctgt gcgtgtgaaa aaagtttgct atggactgtg agctgtgaaa      60
aaatctgctg taggctgtaa gctgttaaaa agctaaaaac cgtttggttg aaaccactaa     120
aagtcgttaa aaattccttc gatatatgtt tcacagttac atccgaaaaa ccactaaaag     180
caggtctaga ggtgctttca gatttgcact acgagaaagt cggcttttag aaaaagttgc     240
ttcctagatc cagccctttg gttggctttt ggcttttagg ggtgcaaaac aaagccaaaa     300
gtcaaacaaa cacacc                                                    316
```

<210> SEQ ID NO 29
<211> LENGTH: 369
<212> TYPE: DNA
<213> ORGANISM: Zea mays

<400> SEQUENCE: 29

```
cacttaggtt ccgtttgttt cttttcattt tgaggaattg gaatcttact aatggattag      60
gctagttttt ttagaatgta acattccacc actttccaaa gttatcatat aagcttatct     120
caaattcatg aggcgagaga tggaaattga ttctatagat ttacatgcta tttttccgat     180
gcacaactta tagcacactc ttctacttgc ttcgctataa cataaatgta gtatataact     240
atctctctca tgatttagga taatatacaa atatattaca tatataaata tacgaattta     300
attagttttg tataaattat aattattaaa atggaattca attccaacga aacaaacggg     360
gccttaagt                                                            369
```

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 30

```
agccagattt tcagaaaagc tg                                              22
```

<210> SEQ ID NO 31
<211> LENGTH: 20
<212> TYPE: DNA
<213> ORGANISM: Artificial Sequence
<220> FEATURE:
<221> NAME/KEY: misc_difference
<222> LOCATION: (20)
<223> OTHER INFORMATION: N can be any nucleotide
<223> OTHER INFORMATION: Description of Artificial Sequence:
      Oligonucleotide primer

<400> SEQUENCE: 31

```
gacgatgagt cctgagtaan                                                 20
```

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 32
gcaacttttt tcacaggcac                    20

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 33
tcacaggcac agctcaac                      18

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 34
tggaaagtgg tggaatgtc                     19

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 35
gattccaatt cctcgaaatg                    20

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 36
ctcaatccag ccctaaccga ac                 22

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 37
actccaatcc ccctcaatcc                    20

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 38

-continued

```
astwagattc caattcctca aaatgaa                                          27

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 39
gacgatgagt cctgagtag                                                   19

<210> SEQ ID NO 40
<211> LENGTH: 20
<212> TYPE: DNA
<213> ORGANISM: Artificial Sequence
<220> FEATURE:
<221> NAME/KEY: misc_difference
<222> LOCATION: (20)
<223> OTHER INFORMATION: N can be any nucleotide
<223> OTHER INFORMATION: Description of Artificial Sequence:
      Oligonucleotide primer

<400> SEQUENCE: 40
gacgatgagt cctgagtagn                                                  20
```

MINIATURE INVERTED REPEAT TRANSPOSABLE ELEMENTS AND METHODS OF USE

CONTINUING APPLICATION DATA

This application claims the benefit of U.S. Provisional Application Ser. No. 60/153,812, filed Sep. 14, 1999, which is incorporated by reference herein.

GOVERNMENT FUNDING

The present invention was made with government support under Grant No. RO1-32528, awarded by the National Institutes of Health. The Government may have certain rights in this invention.

BACKGROUND

Transposable elements are divided into two classes: Class 1, or retro-elements include the most abundant element in plants, the long terminal repeat (LTR) retrotransposons (such as Tnt1, Opie, Huck, and BARE1) and also the long interspersed nuclear elements (LINEs, also known as non-LTR retrotransposons), and short interspersed nuclear elements (SINEs). For all Class 1 elements, it is the element-encoded mRNA, and not the element itself, that forms the transposition intermediate. In contrast, Class 2 or DNA elements are characterized by short terminal inverted repeats (TIRs) and, most importantly, transposition via a DNA intermediate. Plant DNA elements (such as Ac/Ds, Spm/dSpm and Mutator) usually excise from one site and re-insert elsewhere.

A unique Class 2 transposable element was discovered as a 128 base pair insertion in an exon of the maize waxy coding region in the wxB2 mutant allele. Database searches identified related elements (on average about 70% sequence identity) in the introns or the 5' or 3' flanking sequences of many maize coding regions. This new family was called Tourist. Almost one third of all sequenced maize coding regions contain a Tourist element as do the coding regions of other members of the grass tribe including rice, sorghum and barley. An insertion into a Tourist element led to the discovery of another element family called Stowaway, in the coding regions of both monocotyledonous and dicotyledonous plants. Finally, a systematic search of all available rice genomic sequences identified the new element families Gaijin, Castaway, Ditto, Wanderer, Explorer and revealed that short inverted-repeat elements were the predominant repeat sequence associated with rice coding regions (Bureau et al. (1996) *Proc. Natl. Acad. Sci. USA,* 93 8524–8529). These elements formed a unique collection of inverted-repeat transposons referred to as miniature inverted-repeat transposable elements (MITEs).

MITEs have been identified in all flowering plants that have significant genomic nucleotide sequences present in databases. For instance, MITE families have been found in maize, rice (including Gaijin, Castaway, Ditto, Wanderer, Explorer; Snap, Crackle, and Pop), bell pepper (Alien), and alfalfa (Bigfoot). The first MITE family from Arabidopsis, Emigrant, was recently described. Most characterized MITE families in plants appear to be relatively ancient components of genomes since family members were only distantly related to each other (70% sequence identity on average) and insertion sites were usually not polymorphic among members of the same species (Bureau et al. (1992) *The Plant Cell* 4, 1283–1294; Bureau et al. (1994) *Proc. Natl. Acad. Sci. USA,* 91, 1411–1415; Bureau et al. (1994) *The Plant Cell,* 6, 907–916).

MITEs are not restricted to flowering plants. MITE families have been described in insects (*Aedes aegypti,* the yellow fever mosquito), *C. elegans,* and even humans (trigger 1 and 2).

Despite the prevalence of MITEs in plant genomes little is known about their biology including, for instance, their distribution. This largely reflects the fact that most MITEs have been identified through database searches (see, for instance, Bureau et al. (1992) *The Plant Cell,* 4, 1283–1294; Bureau et al. (1994) *Proc. Natl. Acad. Sci. USA,* 91, 1411–1415; Bureau et al. (1994) *The Plant Cell,* 6, 907–916. For this reason, much of what is known about this important class of elements is restricted to MITE identification, categorization and descriptions of their presence in genic regions. It is not currently known, for example, whether their association with coding regions reflects a true target site preference or whether this is merely an artifact of identifying elements by searching the gene-rich databases. Recently, it was shown that in a 225 kilobase region of the maize genome, putative MITEs were found within genic regions, and not in nongenic regions (Tikhonov et al. (1999) *Proc. Natl. Acad. Sci. USA,* 96, 7409–7414) However, 225 kilobases represents less than 0.0001% of total maize DNA, thus it is unclear if these results can be extrapolated to the entire maize genome.

The investigation of genome structure has been accelerated by the use of in vitro methods that detect variation in the DNA sequence in the genomes between members of a species or closely related species. This variation at different locations in the genome is unique for each individual member of a species. These in vitro methods detect the variation, and produce what is referred to as a DNA fingerprint for an individual. Typically, the more closely related two individuals, the more similar the DNA fingerprint from each individual. DNA sequence differences detected by DNA fingerprinting, including single base pair changes as well as large deletions or additions, are referred to as polymorphisms. A polymorphism provides a marker for a specific location on a chromosome in the individual containing the polymorphism. A marker is typically detected as a DNA fragment.

Since the advent of these in vitro methods in the early 1980s, numerous methods for detecting polymorphisms that mark chromosomes have been developed. For instance, restriction fragment length polymorphism (RFLP), DNA amplification fingerprinting, cleaved amplified polymorphisms, randomly amplified polymorphic DNA, arbitrary primed-polymerase chain reaction, random amplified microsatellite polymorphism, simple sequence repeat, amplified fragment length polymorphism (AFLP) (Zabeau, EP Pat. No. 0 534 858 A1) and sequence-specific amplification polymorphisms (Waugh et al. (1997) *Mol. Gen. Genet.,* 253, 687–694) have made their way into use in plant breeding and genetics. In general, the markers that are produced by each of these methods are randomly distributed throughout the genome and allow saturated genome coverage if enough markers are developed.

Typically, genomes contain nongenic regions, i.e., regions that do not contain coding regions. This is particularly true of plants where up to 99.5% of the genome can be nongenic. Nongenic regions are made up of mainly repetitive DNA, i.e., regions of DNA having nucleotides sequences that are present multiple times in the genome. Interspersed in non-genic are regions containing coding regions. These regions are referred to as genic regions and are made up of low or single copy regions of DNA. Typically, a large fraction of the markers generated by in vitro methods that detect variation in the DNA sequence are located in nongenic regions. Consequently, there is an increased cost in generating and mapping excessive numbers of markers.

SUMMARY OF THE INVENTION

The large plant genomes generally contain genes interspersed with much longer blocks of repetitive DNA. Given this organization, it would be highly desirable to have polymorphic markers that are located preferentially in genic regions. It would be even more desirable if these markers were present in high numbers in the genic regions. The present invention discloses that miniature inverted repeat transposable elements (MITEs) are polymorphic markers located preferentially in genic regions. The invention presents the first analysis of the distribution of MITEs that includes an entire genome, i.e., the analysis is not confined to genic regions or to a limited portion of a genome. This analysis indicates that MITEs are preferentially located in genic regions. This analysis of MITEs also unexpectedly showed that MITEs are polymorphic. The polymorphic nature of MITEs was surprising because other transposable elements associated with genic regions, for instance Alu elements in humans, are usually in the same position in all individuals of a species. The polymorphism of MITEs, coupled with their genic preference, indicates that they are a major factor in generating allelic diversity.

An advantage of the methods of the present invention over other in vitro methods that detect DNA variation is that since markers generated using MITEs are preferentially located in genic regions, less markers must be generated and mapped. Thus, costs are decreased. Also, the high copy number of MITEs is expected to allow genic regions to be saturated with markers using the methods of the present invention.

The present invention provides a method of characterizing the DNA of an individual, for instance by producing a DNA fingerprint of an individual. The method includes digesting the DNA of the individual with a restriction endonuclease, ligating a double stranded adaptor to at least one end of the restriction fragments, and amplifying at least a portion of the restriction fragments with a primer pair. Typically, the DNA is genomic DNA. The nucleotide sequence of one primer of the primer pair is complementary to a portion of a miniature inverted repeat transposable element that is a member of a miniature inverted repeat transposable element family, and the other primer of the primer pair includes at the 5' end a nucleotide sequence complementary to at least a portion of the adaptor. The amplified fragments are resolved, typically by electrophoresis, to produce a DNA fingerprint. Optionally, at least about 70% of the miniature inverted repeat transposable elements of the miniature inverted repeat family are present in genic regions Optionally, the individual can be a plant, including maize and teosinte. When the individual is maize, the miniature inverted repeat transposable element can have at least about 90% identity to SEQ ID NO:26, or the complement thereof, at least about 90% identity to SEQ ID NOs:28, or the complement thereof, at least about 90% identity to SEQ ID NO:29, or the complements thereof, or at least about 90% identity to SEQ ID NO:27, or the complement thereof.

Optionally, one of the primers includes a detectable label, for instance a radioactive label, a fluorescent label, a chemiluminescent label, or a combination thereof.

Another aspect of the invention provides a method of detecting at least one polymorphism between the nucleic acid fragments of a first individual and a second individual. The method includes producing a DNA fingerprint of each individual, and comparing the amplified fragments of each individual to detect at least one difference between the amplified fragments of the first individual and the amplified fragments of the second individual. The difference between the amplified fragments of the first individual and the amplified fragments of the second individual indicates the presence of a polymorphism. Optionally, the producing and comparing steps can be repeated with additional individuals, and/or the first individual and second individual can be members of a recombinant inbred line mapping population.

The present invention also provides a method of correlating the presence of an amplified fragment to a phenotype. The method includes producing a DNA fingerprint of a first individual that displays a phenotype, and of a second individual that does not display the phenotype. The amplified fragments of each individual are compared to detect at least one difference between the amplified fragments of the first individual and the amplified fragments of the second individual. The presence of the amplified fragments is then related to the display of the phenotype. Optionally, the producing and comparing steps can be repeated with additional individuals, and/or the first individual and second individual can be members of a recombinant inbred line mapping population.

In another aspect, the invention provides a method for generating a set of molecular markers. The method includes producing a DNA fingerprint of a first individual and a DNA fingerprint of a second individual, where the first and the second individuals are members of different recombinant inbred lines that are members of the same mapping population. The amplified fragments of the first individual and the second individual are compared to detect at least one polymorphism, and the producing and comparing steps are repeated with additional individuals, where the additional individuals are members of different recombinant inbred lines that are members of the same mapping population as the first and second individuals. The linkage between the at least one polymorphism and a set of known markers, for instance, RFLP markers or AFLP markers, is then determined.

DEFINITIONS

"Nucleic acid fragment" as used herein refers to a linear polymeric form of nucleotides of any length, either ribonucleotides or deoxynucleotides, and includes both double- and single-stranded DNA and RNA. A nucleic acid fragment may include both coding and non-coding regions that can be obtained directly from a natural source (e.g., a plant), or can be prepared with the aid of recombinant or synthetic techniques. An example of a nucleic acid fragment present in an individual is a chromosome. A nucleic acid molecule may be equivalent to this nucleic acid fragment or a nucleic acid molecule can include this fragment in addition to one or more other nucleotides. For example, a nucleic acid molecule of the invention can be a vector, such as an expression or cloning vector. A coding region is a linear form of nucleotides that typically encodes a polypeptide, usually via mRNA.

A "restriction fragment" as used herein is a type of nucleic acid fragment. A restriction fragment results from exposing at least one nucleic acid fragment, for instance the genomic DNA of an individual, to a restriction endonulease under conditions such that the restriction endonuclease cleaves the DNA.

An "amplified fragment" as used herein is a type of nucleic acid fragment. An amplified fragment is the result of exposing a nucleic acid fragment to at least two primers under conditions such that the primers hybridize to the nucleic acid fragment and increase the number of the portion of the nucleic acid fragment. The portion of the nucleic acid fragment that is increased is the nucleotides to which the primers hybridize and the region of the nucleic acid fragment located between the nucleotides to which the primers hybridize.

A "DNA fingerprint" as used herein refers to the pattern of nucleic acid fragments that results when an individual's DNA is subjected to an in vitro method that detects variation in the DNA sequence, for instance the methods of the present invention. Typically, the more closely related two individuals, the more similar the DNA fingerprint from each individual. Variations between the DNA fingerprints of two individuals, i.e., the presence or absence of a nucleic acid fragment in one individual compared to another, is referred to as a "polymorphism" or a "polymorphic marker." A polymorphism results from DNA sequence differences, including single base pair changes as well as large deletions or additions, between the two individuals. Such a change in a DNA sequence is typically inherited as expected by Mendel's laws of inheritance. Thus, polymorphisms can be used as genetic markers to map the nucleotides responsible for a phenotype.

As used herein, an "individual" refers to a single entity, for instance, a single plant, or a single animal.

"Phenotype" is a visible or otherwise measurable property of an individual.

"Genomic DNA" refers to the DNA present in a cell of an individual. The DNA includes chromosomal and extrachromosomal, for instance, plastid, DNA.

"Complement" and "complementary" refer to the ability of two single stranded nucleic acid fragments to base pair with each other, where an adenine on one nucleic acid fragment will base pair to a thymine on a second nucleic acid fragment and a cytosine on one nucleic acid fragment will base pair to a guanine on a second nucleic acid fragment. Two nucleic acid fragments are complementary to each other when a nucleotide sequence in one nucleic acid fragment can base pair with a nucleotide sequence in a second nucleic acid fragment. For instance, 5'-ATGC and 5'-GCAT are complementary. The term complement and complementary also encompasses two nucleic acid fragments where one nucleic acid fragment contains at least one nucleotide that will not base pair to at least one nucleotide present on a second nucleic acid fragment. For instance the third nucleotide of each of the two nucleic acid fragments 5'-ATTGC and 5'-GCTAT will not base pair, but these two nucleic acid fragments are complementary as defined herein. Typically two nucleic acid fragments are complementary if they hybridize under the conditions referred to herein.

"Correlating" as used herein refers to determining linkage. Linkage can be determined using genetic methods well known in the art including, for instance, recombination analysis. Linkage can also be determined using physical methods including, for instance, chromosome walking.

"Mapping population" as used herein refers to parents and progeny used to establish genetic linkage. Mapping populations, including mapping populations for mice and plants, are well known to the art.

Unless otherwise specified, the indefinite article "a" or "an" means one or more.

BRIEF DESCRIPTION OF THE FIGURES

FIG. 3. MITEs. A. Nucleotide sequence of Hbr-hm1. TIR refers to terminal inverted repeat; short arrows indicate the position of the flanking direct repeat sequence, thus the element is flanked on each side by 3 nucleotides that are not part of the element. B. Nucleotide sequence B2-waxy. C. Nucleotide sequence alignment of an HB2 element. D. Nucleotide sequence an mPIF element.

FIG. 4. Sequence of a Heartbreaker-hm1 element and location of adaptor and primers. A. Schematic depicting MseI adaptor ligated to one end of a genomic DNA. The nucleotides 5'-TAA and 3'-T and the dashes to the right of the MseI adaptor represent genomic DNA. The location that the MseI+0 primer hybridizes with the MseI adaptor is shown, as is the $T_m$ for the MseI+0 primer. $T_m$ refers to the melting temperature of the interaction between a primer and its complement. Melting temperatures were calculated using the formula $T_m=69.3+0.41(\%GC)-650/L$, where %GC refers to the percentage of G+C in the primer and L refers to the length (in nucleotides) of the primer (Mazars et al., (1991) Nucl. Acids Res., 19, 4783). B. Nucleotide sequence of one strand of a Heartbreaker-hm1 element. The locations that the primers HbrInt5-F and HbrInt5-E hybridize with the element are shown; underlined sequences represent the Terminal Inverted Repeats (TIRs).

DETAILED DESCRIPTION OF THE INVENTION

Figure 1:
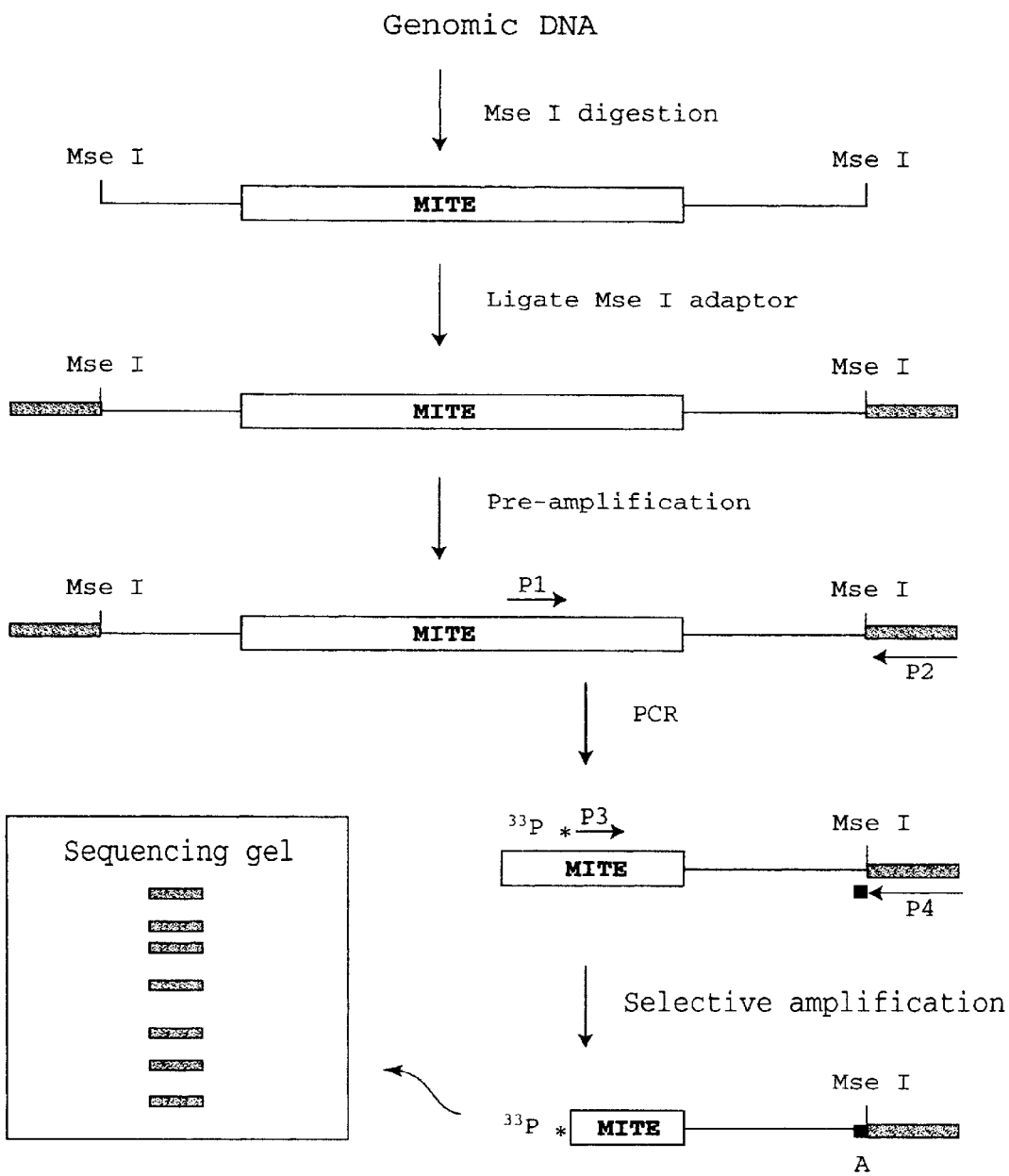
FIG. 1. Schematic of producing a DNA fingerprint. An aspect of the present method is presented. The open box represents a MITE present in an individual's genomic DNA; horizontal line on either side of the MITE represents the individual's genomic DNA; shaded boxes represent adaptors; P1 and P3 represent two MITE-specific primers; P2 refers to a primer complementary to the adaptor, P4 refers to a primer complementary to the adaptor, where P4 has an additional adenine present at the 3' end of the primer, P1 and P2 is a primer pair, P3 and P4 is a primer pair; and the sequencing gel is a schematic of a gel on which the amplified fragments of the selective amplification are resolved. The pattern of the amplified fragments on the gel is the DNA fingerprint.

The present invention provides methods of using miniature inverted repeat transposable elements (MITEs). In one aspect of the invention, methods are directed to producing a DNA fingerprint of an individual. In other aspects of the invention, methods are directed to detecting a polymorphism between the nucleic acid fragments of two individuals. Other methods are directed to correlating the presence of an amplified fragment to a phenotype. The methods include providing a plurality of restriction fragments, and amplifying the restriction fragments with a primer pair. The plurality of restriction fragments is provided by digesting the genomic DNA of the individual with a restriction endonuclease and ligating a double stranded adaptor to the resulting restriction fragments. The nucleotide sequence of one primer of the primer pair is complementary to a portion of a miniature inverted repeat transposable element that is a member of a miniature inverted repeat transposable element, and the other primer of the primer pair includes at the 5' end a nucleotide sequence complementary to at least a portion of the adaptor. After amplification, the amplified fragments can be resolved to produce a DNA fingerprint of the individual.

MITEs typically share many features including their short length from about 125 base pairs to about 500 base pairs; terminal inverted repeats (TIR) of about 10 base pairs to about 15 base pairs, and very high copy number for DNA elements (>1000 per haploid genome).

Typically, a MITE is a member of a MITE family. A MITE family is a group of MITEs having a certain level of nucleotide sequence identity, also referred to as percent identity. The test to determine whether two MITEs are members of the same family is to measure the nucleotide sequence identity between the two MITEs. Nucleotide sequence identity is determined by aligning the nucleotides of the two MITEs to optimize the number of identical nucleotides along the lengths of their sequences; gaps in either or both sequences are permitted in making the alignment in order to optimize the number of shared nucleotides, although the nucleotides in each sequence must nonetheless remain in their proper order. Preferably, the nucleotide sequences of two MITEs are compared using the Blastn program, version 2.0.9, of the BLAST 2 search algorithm, as described by Tatusova, et al. (*FEMS Microbiol Lett* 1999, 174:247–250), and available at the internet address www.ncbi.nlm.nih.gov/gorf/blhtml. Preferably, the default values for all BLAST 2 search parameters are used, including reward for match=1, penalty for mismatch=−2, open gap penalty=5, extension gap penalty=2, gap x_dropoff=50, expect=10, wordsize=11, and filter on. Preferably, unless noted otherwise, two MITEs that are members of a MITE family have, in increasing order of preference, at least about 70%, at least about 80%, at least about 90%, most preferably at least about 95% identity.

While not intending to be limiting, it is expected that higher identity between members of a MITE family (for instance at least about 90% identity) suggests that the members of the MITE family were relatively recently amplified (i.e., recently spread throughout the genome of a species). A MITE family that has recently amplified is expected to have-a higher number of polymorphic insertion sites than a MITE family that has amplified less recently. MITE families with high nucleotide sequence identity also permits the use of relatively long non-degenerate primers, which are described herein.

In addition to having the percent identity described above, MITEs useful in the methods of the present invention typically have several other characteristics. For instance, MITEs are typically (1) present in an individual's genome in high copy number, (2) present predominately in genic regions, and (3) polymorphic.

The copy number of the members of a MITE family in an individual can be measured. For instance, a MITE that is a member of the MITE family can be used to screen a library of genomic DNA (see, for example, Example 1). Typically, a fraction of the clones present in the library are screened, and the number of clones with sequences having the appropriate percent identity with the MITE can be used to extrapolate the copy number of members of a MITE family in an individual. In increasing order of preference, the copy number of the members of a MITE family is at least about 1,000 per haploid genome, at least about 5,000 per haploid genome, at least about 10,000 per haploid genome, most preferably at least about 15,000 per haploid genome.

Typically, a certain percentage of the members of a MITE family are associated with genic regions in the genome of an individual. Whether members of a MITE family are associated with genic or nongenic regions can be tested by cloning an individual MITE from an individual as described herein, identifying the. genomic DNA flanking the MITE, and using the flanking DNA as a probe in a Southern blot of the genomic DNA of the individual. If the flanking DNA hybridizes to no greater than about 10 genomic DNA fragments on the blot, then that MITE is considered to be inserted into a genic region. Preferably, the flanking DNA hybridizes to about 7, more preferably about 4, most preferably about 1 genomic DNA fragment on the blot. Typically, this process is repeated for about 25 randomly isolated individual MITEs of the same MITE family, and the percentageof MITEs that are members of a MITE family present in genic regions is determined. Preferably, about 70%, more preferably about 75%, most preferably about 80% of the MITEs of a MITE family are present in genic regions.

Optionally, the nucleotide sequence of the flanking DNA can be determined and used to query databases, for instance GenBank, for similar nucleotide sequences using algorithms well known to the art, for instance BLAST. If the flanking DNA is similar to a known coding region, or if there is no similar DNA sequence in the database, then the MITE is considered to be inserted in a genic region. This process is repeated for about 25 randomly isolated individual MITEs of the same MITE family, and the percentage of MITEs having flanking DNA that is similar to a coding region in databases or not similar to any nucleotide sequences in databases is determined. Preferably, about 70%, more preferably about 75%, most preferably about 80% of the MITEs of a MITE family are present in genic regions. A method for determining the percentage of members of a MITE family that are associated with genic regions is shown in Example 1.

Typically, MITEs useful in the present invention are polymorphic. Tests to evaluate polymorphism are described herein.

It is expected that an individual that contains MITEs in its genome can be used in the present invention The individual can be an animal or a plant, preferably a plant. The plant can be a monocot plant or a dicot plant, preferably a monocot plant. Without intending to be limiting, examples of monocot plants include grass species such as maize, wheat, barley, millet, rice, sorghum, teosinte, Coix, and Tripsacum. Other plants include, for instance, soybean, tomato, pepper, cotton, peach, cherry, apple, and potato. Preferably, when the methods are directed to detecting a polymorphism between the nucleic acid fragments of two individuals, or directed to correlating the presence of an amplified fragment to a phenotype, the two individuals are the same species.

The DNA that is to be characterized in some of the methods of the present invention can be genomic DNA isolated from an individual. Methods for isolating genomic DNA from an individual vary depending on the type of individual, and these methods are well known to the art (see, for instance, Sambrook et al, (1989) *Molecular Cloning: A Laboratory Manual.,* Cold Spring Harbor Laboratory Press; McCouch et al. (1988) *Theor. Appl. Genet.,* 76, 815–829). The genomic DNA can be isolated from a biological source including, for instance, an individual, tissue isolated from an individual, a cell isolated from the individual, a cell cultured from the individual, a recombinant prokaryotic or eukaryotic cell that contains a nucleic acid fragment (for instance a chromosome) from the individual, or an egg or a seed from the individual.

cDNAs can be the source of the DNA that is to be characterized. Optionally, the cDNAs can be present as clones in a library. Methods to produce cDNAs and clone cDNAs into vectors to construct a library are well known to the art.

Examples of MITE families that can be used in aspects of the present methods include MITE families that are know to the art. It is expected that other MITEs that have not yet been characterized will be useful in the present invention. A MITE family useful in aspects of the present invention when the individual is maize or teosinte is the MITE family Heartbreaker (Hbr). Hbr is typically at least about 310 nucleotides in length and typically not greater than 318 nucleotides in length. There are typically about 3000–4000 Hbr elements per maize haploid genome. Typically, Hbr elements have at least about 90% identity, more preferably at least about 92% identity, most preferably about 95% identity. Typically, greater than about 75% of the members of the Hbr family are present in genic regions. An example of a member of the Hbr family of MITEs is shown in FIG. 3A.

Another MITE family useful in aspects of the present invention when the individual is maize or teosinte is the MITE family Hb2. The founding member of this family was a previously isolated insertion upstream of the maize waxy gene promoter. Hb2 is typically at least about 310 nucleotides in length and typically not greater than 320 nucleotides in length. There are typically about 12,000 Hb2 elements per maize haploid genome. Typically, Hb2 elements have at least about 90% identity, more preferably at least about 92% identity, most preferably about 95% identity. Typically, greater than about 75% of the members of the Hb2 family are present in genic regions. An example of a member of the Hb2 family of MITEs is shown in FIG. 3C.

A third example of a MITE family useful in aspects of the present invention when the individual is maize or teosinte is the MITE family mPIF. mPIF is typically at least about 350 nucleotides in length and typically not greater than 365 nucleotides in length. There are typically about 12,000 mPIF elements per maize haploid genome. Typically, mPIF elements have at least about 90% identity, more preferably greater than 90% identity. Typically, greater than about 75% of the members of the mPIF family are present in genic regions. An example of a member of the mPIF family of MITEs is shown in FIG. 3D.

A fourth example of a MITE family useful in aspects of the present invention when the individual is maize or teosinte is the MITE family B2. B2 is typically at least about 120 nucleotides in length and typically not greater than 140 nucleotides in length. There are typically about 2,000 B2 elements per maize haploid genome. Typically, B2 elements have at least about 90% identity, more preferably greater than 90% identity. Typically, greater than about 75% of the members of the B2 family are present in genic regions. An example of a member of the B2 family of MITEs is shown in FIG. 3B.

MITE families can also be identified using methods well known to the art including computer analysis of genome nucleotide sequences in databases (see, for instance, Bureau et al., (1996) *Proc. Natl. Acad. Sci. USA* 93, 8524–8529; Oosumi et al. (1995) *Nature,* 378, 672; Oosumi et al. (1996) *J. Mol. Evol.,* 43, 11–18; Osborn et al. (1997) *Genet.,* 146, 1123–1129). A well known biochemical method that is expected to allow the identification of MITE families is the measurement of reassociation kinetics, generally referred to as $C_{o}t$ analysis. $C_{o}t$ analysis provides an estimate of genome size, the amount of single-copy and repetitive sequences, the fraction of the genome occupied by each frequency component, and the complexity of the sequences in each component. However, $C_{o}t$ analysis not only provides information about genomic fractions, it also serves as a biochemical technique to isolate those fractions from total genomic DNA. Thus, it is expected that individual MITEs can be isolated using $C_{o}t$ analysis and the nucleotide sequence of the MITEs determined and used as described herein. Detailed descriptions of the methodology of $C_{o}t$ analysis are available (Britten et al. (1974) *Meth. Enzymol.,* 29, 363–418).

Once an individual MITE is identified in an individual, the MITE can be used to determine if the MITE is a representative of a MITE family in the individual. One method to identify other closely related MITEs within the individual includes using the MITE to screen a library of genomic DNA from the individual, for instance as is described in Example 1. The nucleotide sequence of cloned MITEs identified in the screen can be determined and their percent identity determined. An alternative, rapid method for obtaining the sequences of many MITE family members involves PCR amplification of genomic DNA using primers that are complementary to the TIRs present in a MITE. The primers amplify MITEs, which can be cloned and the nucleotide sequence of the MITE determined. Methods for determining the nucleotide sequence of primers that are complementary to the TIRs of a MITE family are described herein.

The restriction endonuclease used to digest the DNA in some aspects of the methods of the present invention can be Type I or Type II, preferably Type II. Type II restriction endonucleases typically recognize between at least four nucleotides and up to about eight nucleotides. Preferably, the restriction endonuclease recognizes four nucleotides. The nucleotides are typically palindromic, and the cleavage site is typically within the recognition site. Preferred restriction endonucleases are MseI and BfaI.

The adaptors used in the present invention are typically designed such that they contain enough nucleotides to allow the use of primers of sufficient length such that the primer is specific for the adaptor and does not bind other nucleotides present in the individual's DNA. An adaptor is generally about 15 nucleotides to about 20 nucleotides in length, but shorter or longer adaptors can be used. Typically, an adaptor has one blunt end or a sticky end that is ligated to a restriction fragment. SEQ ID NO:23 is an example of an adaptor that can be used.

Two types of primers are used in aspects of the methods of the present invention. The nucleotide sequence of one type of primer is complementary to a portion of the nucleotide sequence of a MITE, and another type of primer includes at the 5' end a nucleotide sequence complementary to at least a portion of an adaptor. The combination of these two types of primers is referred to as a primer pair. When used in combination and under the appropriate conditions, these two types of primers can result in the selective amplification of an individual's DNA, where the resulting amplified fragments include at least a portion of a MITE and at least a portion of the adaptor. Typically, an individual's DNA is amplified using a single primer pair. Optionally and preferably, an individual's DNA is amplified using two primer pairs in two separate amplification reactions; a first primer pair (which includes a first primer and a second primer) is used to pre-amplify an individual's DNA to result in a population of amplified fragments, and a second primer pair (which includes a third primer and a fourth primer) is used to amplify the amplified fragments. In general, the process of identifying primer pairs that function in aspects of the methods of the present invention is trial and error, and time consuming. How to determine whether a primer pair functions in aspects of the methods of the present invention is described herein.

The first primer and third primer can be complementary to a portion of the nucleotides of a TIR, a portion of the nucleotides of the region between the two TIRs, a portion of the nucleotides of both a TIR and the region between the two TIRs, or a complement thereof.

In order to design a first primer or third primer useful in aspects of the present invention, the nucleotide sequence of members of a MITE family are determined to identify regions, preferably a region of at least 20 nucleotides, of a certain percent identity. For instance, the nucleotide sequences of MITEs identified as described herein can be aligned and regions of a certain percent identity can be identified by comparing pairs of MITEs as described herein. Preferably, the percent identity of a region of nucleotides is at least about 90%, more preferably at least about 92%, most preferably at least about 94% identity between all the aligned MITEs. These regions can then be used to identify candidate first primers and third primers. Typically, the nucleotide sequences of about 5 to about 20 individual MITEs are determined and aligned. Preferably, the nucleotide sequence of the first primer and third primer is non-degenerate. Preferably, the nucleotide sequence of the first primer and third primer is at least about 18 nucleotides in length.

Typically, a first primer and third primer hybridize to members of the MITE family and do not hybridize to members of other MITE families. Thus, when for instance a first primer is used in a primer pair, the primer pair does not cause amplification of members of other MITE families. For instance, a first primer that hybridizes to and causes amplification of a member of the Hbr family does not hybridize to and cause amplification of a member of the Hb2, mPIF, or B2 families. This can be tested by identifying an individual whose genomic DNA does not contain the MITE family that the first primer is designed to hybridize to, and then, using the methods of the present invention, testing whether the first primer causes amplification of the genomic DNA of that individual. To be useful in the methods of the present invention, a first primer and a third primer do not have to amplify all members of the MITE family.

An individual that does not contain the MITE family can be identified using methods well known in the art. For instance, an individual MITE that is a member of the MITE family can be used as a probe. If the probe does not hybridize to the genomic DNA of an individual under high stringency conditions, then the individual does not contain the MITE family. Determining high stringency conditions for the hybridization of a probe to nucleic acid fragments is well known to the art. An example of the use of a MITE to probe the genomic DNA of an individual is detailed in Example 1.

The nucleotide sequence of a second primer (which is used in combination with a first primer) is complementary to at least a portion of the adaptor ligated to the restriction fragments generated in some aspects of the methods of the invention. Typically, a second primer is about the same length as the first primer with which it is paired. Typically, a second primer and the first primer with which it is paired have about the same annealing temperature. The annealing temperature of a primer can be determined by methods well known to the art (see, for instance, Mazars et al. (1991 ) Nucl. Acid Res., 19, 4783).

The nucleotide sequence of a fourth primer (which is used in combination with a third primer) is complementary to at least a portion of the adaptor ligated to the restriction fragments generated in some aspects of the methods of the invention. Optionally and preferably, a fourth primer has, in addition to a nucleotide sequence complementary to the adaptor, between one to four additional nucleotides at the 3' end of the primer, more preferably, one additional nucleotide. The addition of between one to four additional nucleotides at the 3' end of the primer does not result in the primer being a degenerate primer. The presence of at least one additional nucleotide at the 3' end typically decreases the number of amplified fragments that result from an amplification reaction. A fourth primer having at least one additional nucleotide at the 3' end of the primer is useful when altering amplification conditions to result in an optimal number of amplified fragments is described herein. Typically, a fourth primer is about the same length as the third primer with which it is paired. Typically, a fourth primer and the third primer with which it is paired have about the same annealing temperature.

The choice of the nucleotide sequence of a primer pair also depends on the number of amplified fragments that result from using the primer pair in amplification reactions. Since resolution of individual amplified fragments allows detection of polymorphisms, typically a primer pair is chosen that results in a number of amplified fragments that can be individually resolved. Typically, the appropriate number of amplified fragments depends on the resolution method used.

Whether a primer pair functions to amplify DNA can be determined by using the primer pair to amplify the DNA of an individual containing members of the MITE family to which the first primer and third primer are designed to hybridize. A primer pair that can be used in the present methods produces an individual-specific, reproducible pattern of amplified fragments (i.e., a DNA fingerprint).

Typically, the members of a MITE family to which the first primer and third primer hybridize are polymorphic in an individual, i.e., it is not present in the same location of the genome in all the individuals in a species. Whether a MITE family is polymorphic can be determined using the methods of the invention. The genomic DNA used in this test is isolated from two individuals that are not genetically identical. For instance, if the individual is a plant, two plants having different phenotypes can be used. Preferably, the two plants can be members of a mapping population, for example B73×Mo 17 in maize. Preferably, the two individuals are known to have polymorphisms relative to each other as determined by in vitro methods that detect variation in a DNA sequence, for instance RFLP or AFLP.

After the DNA is amplified and resolved as described herein, the resulting amplified fragments are compared. A polymorphic amplified fragment is one that is present in the amplified DNA of one individual and not present in the other individual. A primer pair is considered to be successful when at least one amplified fragment is polymorphic between two individuals. Typically, a useful primer pair results in substantially more than one polymorphic amplified fragment.

When the adaptor shown in SEQ ID NO:23 is used as the adaptor in the methods of the present invention, an example of first and second primers that can be used to amplify the nucleic acid fragments of an individual containing members of the Hbr MITE family are 5' GATTCTCCCCACAGCCA-GATTC (SEQ ID NO:24) and 5' GACGATGAGTCCT-GAGTAA (SEQ ID NO:25), respectively. Examples of third and fourth primers that can be used to amplify the nucleic acid fragments of an individual containing members of the Hbr MITE family are AGCCAGATTTTCAGAAAAGCTG (SEQ ID NO: 30) and 5' GACGATGAGTCCTGAGTAAN (SEQ ID NO:3 1), respectively. The nucleotide sequence of the fourth primer is non-degenerate, i.e., the base labeled N is either an adenine in the primer used, or a guanine, a cytosine, or a thymidine, and not a mixture of the four bases.

When the adaptor shown in SEQ ID NO:23 is used as the adaptor in the methods of the present invention, an example of first and second primers that can be used to amplify the nucleic acid fragments of an individual containing members of the Hb2 MITE family are 5' TCACAGGCACAGCT-CAAC (SEQ ID NO: 33) and 5' GACGATGAGTCCTGAG-TAA (SEQ ID NO:25), respectively. Examples of third and fourth primers that can be used to amplify the nucleic acid fragments of an individual containing members of the Hb2 MITE family are 5' GCAACTTTTTTCACAGGCAC (SEQ ID NO:32) and 5' GACGATGAGTCCTGAGTAAN (SEQ ID NO:31), respectively. The nucleotide sequence of the fourth primer is non-degenerate, i.e., the base labeled N is either an adenine in the primer used, or a guanine, a cytosine, or a thymidine, and not a mixture of the four bases.

When the adaptor shown in SEQ ID NO:23 is used as the adaptor in the methods of the present invention, an example of first and second primers that can be used to amplify the nucleic acid fragments of an individual containing members of the mPIF MITE family are 5' GATTCCAATTCCTC-GAAATG (SEQ ID NO: 35 and 5' GACGATGAGTCCT-GAGTAA (SEQ ID NO:25), respectively. Examples of third and fourth primers that can be used to amplify the nucleic acid fragments of an individual containing members of the mPIF MITE family are 5' TGGAAAGTGGTGGAATGTC (SEQ ID NO: 34), and 5' GACGATGAGTCCTGAGTAAN (SEQ ID NO:31), respectively. The nucleotide sequence of the fourth primer is non-degenerate, i.e., the base labeled N is either an adenine in the primer used, or a guanine, a cytosine, or a thymidine, and not a mixture of the four bases.

When the adaptor shown in SEQ ID NO:23 is used as the adaptor in the methods of the present invention, an example of third and fourth primers that can be used to amplify the nucleic acid fragments of an individual containing members of the B2 MITE family are 5° CTCAATCCAGCCCTAAC-CGAAC (SEQ ID NO:36 and 5' GACGATGAGTCCT-GAGTAAN (SEQ ID NO:31), respectively. Examples of first and second primers that can be used to amplify the nucleic acid fragments of an individual containing members of the B2 MITE family are 5' ACTCCAATCCCCCT-CAATCC (SEQ ID NO: 37 and 5' GACGATGAGTCCT-GAGTAA (SEQ-ID NO:25), respectively. The nucleotide sequence of the fourth primer is non-degenerate, i.e., the base labeled N is either an adenine in the primer used, or a guanine, a cytosine, or a thymidine, and not a mixture of the four bases.

The amplification of DNA is well known to the art, and the method of amplification is not critical in the practice of the present invention. Preferably, the polymerase chain reaction (PCR) is used. It is standard practice in determining the appropriate conditions for PCR with two primers to vary the elongation temperature and/or the annealing times in the amplification reaction. Optionally, methods to increase the specificity of the amplification process, for instance touchdown PCR (Don et al. (1991) *Nucl. Acid Res.,* 19, 4008), or hot start PCR, can be used.

Amplified fragments are typically characterized using standard methods for fractionating nucleic acid fragments. Standard methods include resolving the nucleic acid fragments by-size and detecting the nucleic acid fragments. Typically, the fragments are resolved by electrophoresis in a matrix, preferably polyacrylamide, or agarose, or a mixture of the two. Detection can be by staining, including for instance ethidium bromide. Alternatively, a detectable label can be incorporated into the amplified fragment. The amplification of nucleic acid fragments can be done in the presence of a detectably labeled deoxyribonucleotide (dNTP) Preferably, a primer used in producing the amplified fragment can be labeled with a detectable label. The detectable label can be a radioactive label, a fluorescent label, a chemiluminescent label, or a combination thereof. Radioactive labels preferably include isotopes emitting alpha, beta, or gamma radiation, more preferably radioactive labels are $P^{32}$, $P^{33}$, $S^{35}$, or $I^{125}$, to name a few. Fluorescent labels preferably include, for instance, fluorescein and its derivatives, rhodamine and its derivatives, dansyl, and umbelliferone, to name a few. Suitable chemiluminescent labels that can be used in accordance with the present invention include, for example, luciferin and 2,3-dihydrophthalazinediones, for instance luminol. Methods of detecting labels are well known to the art. Since the primers chosen are typically specific for a particular MITE family, it is expected that the numbers of markers visualized in a single lane can be increased through the simultaneous use of primers to two or more different MITE families, where each primer is labeled with a different fluorescent detectable label. Preferably, a fluorescent detectable label is used when the methods of the present invention are directed to producing a DNA fingerprint or directed to detecting a polymorphism between the nucleic acid fragments of two individuals.

The methods of the present invention can be used in conjunction with other methods of genetic analysis and genome analysis that are well known to the art. For example, the methods of the present invention can be used to produce DNA fingerprints that can be used to determine the relationship between individuals, for instance between members of a species or closely related species. For instance, the methods of the present invention can be used by plant breeders to prevent theft of their plant stocks.

The methods of the present invention can be used to relate the presence of an amplified fragment to a phenotype. For example, plants having a desired phenotype can be compared to the same plant that does not have the desired phenotype. Typically, this process includes the analysis of a population of individuals, including parents and many offsping. An amplified fragment that is present in plants having the desired phenotype and not present in plants without the phenotype can be identified and the linkage of the nucleotide sequences in the amplified fragment to the nucleotide sequences responsible for the phenotype determined using genetic techniques well known to the art. The amplified fragment can be isolated, and the DNA flanking the MITE can be used to aid in determining linkage by genetic techniques, or to begin a chromosome walk to the nucleotide sequence responsible for the desired phenotype. If the nucleotide sequence of the genome of the species being analyzed has been determined, the nucleotide sequence of the DNA flanking the MITE can be determined and used to determine the location of the MITE, or the identity of the coding region in which the MITE resides.

As is shown in Example 2, the methods of the present invention can also be used to create genetic maps (i.e., linkage groups) and aid in the production of physical maps by identifying markers in, for instance, mapping populations. For example, the present methods can be used by crossing members of mapping populations to result in recombinant inbred lines, and then using genetic analysis to map MITEs and establish a set of markers in predominantly genic regions. Preferably, the markers produced using the methods of the present invention are mapped relative to other known markers, for instance RFLP markers or AFLP markers, using methods known to the art. For instance, the present invention is also directed to a method for generating a set of molecular markers. The method includes producing a DNA fingerprint of a first individual and a DNA fingerprint of a second individual, where the first and the second individuals are members of different recombinant inbred lines that are members of the same mapping population. The amplified fragments of the first individual and the second individual are compared to detect at least one polymorphism, and the producing and comparing steps are repeated with additional individuals, where the additional individuals are members of different recombinant inbred lines that are members of the same mapping population as the first and second individuals. The linkage between the at least one polymorphism and a set of known markers, for instance, RFLP markers or AFLP markers, is then determined.

The present invention is illustrated by the following examples. It is to be understood that the particular examples, materials, amounts, and procedures are to be interpreted broadly in accordance with the scope and spirit of the invention as set forth herein.

EXAMPLE 1

Characterization of the Heartbreaker (Hbr) family of MITEs

This example demonstrates that members of the of the Hbr Family of MITEs present in maize have high structural similarity, that the insertion sites of the MITEs are polymorphic, and that the insertions are preferentially in genic regions.

Materials and Methods

Plant Material and Genomic DNA Extraction. Maize strain GH94-1062 (containing Hbr-hm1) was provided by Guri Johal (University of Missouri). Hbr-hm1, discovered as a 314-base pair insertion in the 3' untranslated region of a mutant allele of the maize HM1 gene designated hm1-1062, is flanked by the direct repeat TTA and has a 14-bp terminal inverted repeat (TIR) that is 80% similar to the TIR of the first discovered MITE family Tourist. The internal sequence of Hbr-hm1 is not related to any previously characterized transposable element.

Maize inbred lines 4722, A554, AC88, AM48, B73, B79, C13, W23 were obtained from the USDA-ARS Plant Introduction Station at Ames, Iowa. The following teosinte plants were also used: sorghum (*S. bicolor*), obtained from the USDA-ARS Plant Introduction Station at Ames, Iowa; rice strain IR36, obtained from Gary Kochert (Department of Botany, University of Georgia, Athens); Coix; obtained from Lane Arthur (Department of Botany, University of Georgia, Athens) *Zea parviglumis, Z. mexicana, Z. huehuetenangensis, Z. diploperennis,* and *Z. luxurans, Tripsacum dactyloides* and *T. maizar;* obtained from Sylvestre Marillonnet (Department of Botany, University of Georgia, Athens).

Plant DNA isolation was as described previously (McCouch, S. R. et al. (1988) *Theor. Appl. Genet.,* 76 815–829) using 5 grams of young leaf tissue as the starting material. Briefly, tissue was ground to a fine powder in liquid nitrogen. The powder was mixed with urea-phenol extraction buffer and incubated at 65° C. for 30 minutes. The mixture was then extracted with chloroform.

Southern Blot Analysis. To determine if there are additional copies of Hbr-hm1 in the genome, this element was used to probe a Southern blot containing genomic DNA from the following grasses: B79 (a maize inbred line), *Z. parviglumis, Z. diploperennis, T. dactyloides, T. maizar,* sorghum, Coix, and rice. Ten $\mu$g of genomic DNA from maize, teosinte, Tripsacum and Coix, and 3 $\mu$g from rice and sorghum was digested with HindIII, resolved on an agarose gel, and transferred to a filter. Hbr-hm1 was labeled by extending the primer Hbr-hm1 5' TIR (SEQ ID NO:1) derived from the terminal inverted repeat of Hbr-hm1 with Klenow fragment (Bethesda Research Laboratories) in the presence of $^{32}$P dNTPs.

Southern blot hybridization was performed as described (Zhao, X. et al. (1992) *Mol. Gen. Genet.,* 231, 353–359). Hybridization was carried out at 60° C. in 50 mM Tris (pH 7.5), 1% SDS, 1 M NaCl and denatured salmon sperm DNA (200 $\mu$g/ml) for about 12 hours. The filters were washed in either 2×SSC (20×SSC contains 3 M NaCl and 0.3 M trisodium citrate, pH 7.0), 0.1% sodium dodecyl sulfate (SDS) at 60° C. for 45 minutes (moderate stringency), or in 0.1×SSC, 0.5% SDS at 67° C. for one hour (high stringency).

Hybridization to hundreds or thousands of bands was evident at moderate stringency in maize, teosinte and Tripsacum. No hybridization signal was detected from the genomic DNA the other grasses Coix, sorghum or rice. This suggests a narrow species distribution of the Hbr family.

Polymerase Chain Reaction (PCR). PCR was carried out in 20 $\mu$l containing 10 $\mu$g genomic DNA, 10 mM Tris-Cl (pH 8.3), 50 mM KCl, 1.5 mM MgCl$_2$ and 0.01% gelatin with 200 $\mu$M of each dNTP (Pharmacia), 70 ng of each primer and 2.5 units of polymerase (Ampli Taq; Perkin-Elmer-Cetus). Thirty five cycles of amplification were carried out using a step program (95° C., 1 minute; annealing, 2 minutes; 72° C., 1 minute), followed by 10 minute at 72° C. Table 1 summarizes the sequences of primers used in this study and their annealing temperatures.

TABLE 1

PCR Primers Used in this Study

| Primer | Sequence (5' to 3') | T*(° C.) | SEQ ID NO: |
|---|---|---|---|
| Hbr-hm1 5' TIR | GGGTCTGTTTGGTT | 60 | 1 |
| Hbr-hm1 3' TIR | GGGCCTGTTTGTTT | 60 | 2 |
| H7forward | GCAGTCAGTCCGTCATCCTTG | 58 | 3 |
| H7reverse | ATCCTTGCCTGAAAGCAGCG | 58 | 4 |
| H14forward | GTGCATCAATCTCCAAAATC | 56 | 5 |
| H14reverse | TCAACGTTTCCTAGACGG | 56 | 6 |
| H15forward | TCCAATACGTAAACAGTGC | 54 | 7 |
| H15reverse | CTATTAGCCACTTGGTGC | 54 | 8 |
| H22forward | TCTTTTGGCTCTTTGAGAC | 55 | 9 |
| H22reverse | CGATCAGATACTAGGGCATAC | 55 | 10 |
| H24forward | TCATCTCCGCTTTGCGTAGC | 62 | 11 |
| H24reverse | TGAAACGAGGATCTAATCCTATCCG | 62 | 12 |
| H36forward | AGCCTAAAGGGTTCCTTG | 60 | 13 |
| H36reverse | TTTGAAGCCAGCATCTTG | 60 | 14 |
| H43forward | CTGTCCACCCATCAAATC | 58 | 15 |
| H43reverse | TGTGTTCTTGTCTGTTCCAG | 58 | 16 |
| H48forward | TCCTGGCATCATCAGCTTC | 56 | 17 |
| H48reverse | GCCGCTCTCGTAGTAGAACTTG | 56 | 18 |
| H50forward | ACCGCAGCACTTTAACACAAG | 64 | 19 |
| H50reverse | TGGAAATGAGGATGCCGAC | 64 | 20 |
| H65forward | CGTACCCTAAGGCTCCACAAG | 56 | 21 |
| H65reverse | CCGAGGTTATAGTAGGACCGTAATTAG | 56 | 22 |

*Optimal Annealing Temperature

Figure 2A:
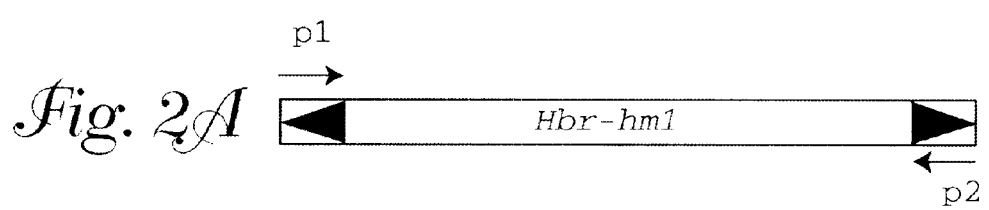
FIG. 2. Amplification of genomic Hbr elements. A. Position of PCR primers (P1 [SEQ ID NO:1] and P2 [SEQ ID NO:2]). Filled rectangles represent the TIRs of Hbr-hm1. B. Agarose gel of the PCR products. M, 100 base pair ladder; B79 and W23, maize lines; Z. parvi., Z parviglumis; Z. dip., Z. diploperennis. C. Autoradiograph of PCR products hybridized with the Hbr-hm1 probe.
Figure 2B:
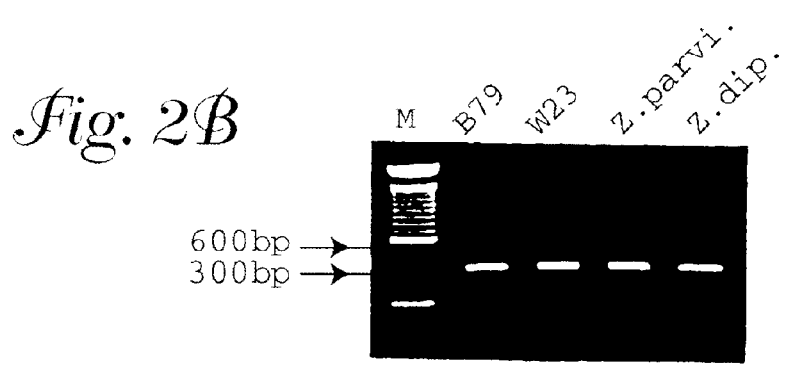
Figure 2C:

To rapidly determine if Hbr-hm1 is a member of a larger MITE family, genomic DNA from two maize inbred lines and from two teosinte strains were amplified by PCR, using the 14-bp TIR of Hbr-hm1 as primers (SEQ ID NOs:1 and 2). PCR products were blotted and probed with labeled Hbr-hm1 (FIG. 2B). The approximately 300 nucleotide product contains sequences that are highly related to the Hbr-hm1 element as demonstrated by the strong hybridization signals seen in all lanes after high stringency washing of the filters (FIG. 2C).

In order to evaluate the degree of similarity between different Hbr-hm1 elements, PCR products amplified, using the Hbr-hm1 5'TIR primer and the Hbr-hm1 3'TIR primer, from the maize inbred line B79 were cloned and eleven independent inserts were sequenced. Each of the eleven products was unique but shared at least 93% sequence identity. As expected, all had identical TIRs since these served as the primers for amplification. That deletions, insertions and point mutations were detected upon comparison of the sequences suggested that the eleven products originated from different elements.

Genomic Library Construction and Screening. To construct a genomic library with inserts of approximately 1 kilobase (referred to as a small insert library), DNA from maize strain GH94-1062 was first partially digested with BamHI and BglII. Briefly, about 15 µg of maize genomic DNA was digested with 10 units of BamHI and 10 units of BglII at 37° C. for 15 minutes. The Hbr-hm1 element does not contain either a BamHI or a BglII site. The DNA was precipitated and then samples were then treated with 5 units of Sau3AI (which has one site in Hbr-hm1) at 37° C. for a period of time to maximize the number of fragments of about 1 kilobase in size. DNA fragments of 0.6 to 1.5 kb were recovered from an agarose gel and purified using a Qiagen gel extraction kit. The compatible BamH1, BglII and Sau3A1 ends were cloned into the Lambda Uni-ZAP XR vector (Stratagene) that had been predigested with BamHI. Ligated phage were packaged (Gigapack Gold, Stratagene) using the manufacturer's suggested conditions and used to infect the strain provided with the kit. The library contained about $7.5 \times 10^5$ plaques (corresponding to about $7.5 \times 10^5$ kilobases (kb) of maize genomic DNA), or about 30% of the maize genome ($7.5 \times 10^5$ kb/ $2.5 \times 10^6$ kb$\times$100=30%).

To determine if the library was representative of the maize genome, about $1.3 \times 10^4$ plaques were probed with the maize retrotransposon Opie-3 (obtained from Jeff Bennetzen (Purdue University), assession number AF050452, AF050453), an element known to comprise about 10% of maize genomic DNA. The copy number of Hbr elements was determined by probing the equivalent of 20% of the maize genome ($5 \times 10^5$ plaques, covering about $5 \times 10^5$ kb of genomic DNA) with labeled Hbr-hm1 DNA. Opie-3 DNA and Hbr-hm1 DNA was labeled by random primer labeling.

Approximately 10% of the plaques hybridized with the Opie-3 probe indicating that the library contained a fair representation of the repetitive sequences in the maize genome. At moderate stringency, 786 plaques hybridized with the Hbr-hm1 probe while 657 plaques were detected using conditions of high stringency. Based on these values, the copy number of Hbr elements per haploid maize genome was estimated to range from 3,000 (high stringency, 657/0.2=3,285) to 4,000 (moderate stringency, 786/0.2=3,930) copies.

Sequence analysis of Hbr elements. As a first step toward comparing element sequences and insertion sites, thirty positive clones were chosen at random (from the moderate stringency condition screen) and both strands of the insert DNA were sequenced. Twenty seven inserts contained Hbr elements with greater than 82% identity with Hbr-hm1. Inserts from the remaining three clones contained partial Hbr sequences. Twenty four of the 27 "complete" elements were 312 to 316 bp and displayed greater than 90% sequence identity. The remaining three elements share 77% to 89% sequence identity with other Hbr elements and with each other. When each Hbr element was compared with a consensus Hbr sequence derived from the above 27 elements, 14 were found to be more than 95% identical, and 10 were found to be 90 to 94% identical. That these elements were chosen at random from the moderate stringency screen suggests that most of the 3000–4000 Hbr elements in the maize genome are highly conserved in both length and sequence.

Isolation of DNA flanking Hbr elements. Genomic DNA flanking Hbr elements was obtained following amplification of the positive clones isolated from the small insert maize genomic library by PCR amplification. Amplification of the positive clones was accomplished using either the Hbr-hm1 5'TIR primer (SEQ ID NO:1) or Hbr-hm1 3'TIR primer (SEQ ID NO:2) with either a T3 or a T7 vector sequences (Stratagene). These sequences flanking the Hbr elements were labeled for use as probes of Southern blots by including $^{32}$P dNTPs in these PCR amplifications. Hybridization was carried out under the same conditions as described above. Hybridized Southern blots were washed either with 2×SSC, 0.1% SDS at 60° C. for one hour (moderate stringency), or with 0.1×SSC, 0.5% SDS at 67° C. for one hour (high stringency).

Sequence analysis of DNA flanking Hbr elements. All templates were sequenced by the Molecular Genetics Instrumentation Facility (University of Georgia, Athens). Maize genomic DNA flanking Hbr elements was compared at the nucleotide level to the 341,073 expressed sequence tag (EST) sequences residing in Pioneer Hi-Bred's (PHI) most comprehensive database (CORNSEQ) using the BlastN 2.0 algorithm to search for similarities. All score and probability results are reported in Table 2.

TABLE 2

Database Search Results Using Hbr Flanking Sequences as Queries

| Query | Match | # of hybridization bands |
|---|---|---|
| Hbr06 flk | None | ND |
| Hbr07 flk | None | 1 |
| Hbr10 flk | Maize DNA for tbp1 gene; Sorghum bicolor ADP-glucose pyrophosphorylase subunit | >10 |
| Hbr11 flk | Maize DNA for Ds123 controlling element; Z. luxurians DNA for Ds1 transposable element; 1 unknown maize gene, maize ruq66 transposon | 2 |
| Hbr12 flk | None | 1 |
| Hbr14 flk | None | 3 to 4 |
| Hbr15 flk | 1 unknown maize gene | 7 to 8 |
| Hbr21 flk | 3 unknown maize contigs | ND |
| Hbr22 flk | 1 unknown maize gene | 2 to 4 |
| Hbr23 flk | None | 1 |
| Hbr24 flk | None | 4 to 5 |
| Hbr25 flk | None | ND |
| Hbr27 flk | 2 unknown maize genes | >10 |
| Hbr29 flk | 1 unknown maize gene | smear |
| Hbr30 flk | Maize 22kD alpha-zein gene | ND |
| Hbr32 flk | 2 unknown maize genes | 2 to 4 |
| Hbr34 flk | None | 1 to 2 |
| Hbr35 flk | Rice 3 delta 1-pyrroline-5-carboxylate synthetase | ND |
| Hbr36 flk | 1 unknown maize gene | 1 to 2 |
| Hbr38 flk | None | 10 |
| Hbr39 flk | Maize transposable element Ac; 3 unknown maize genes | ND |
| Hbr40 flk | None | ND |
| Hbr42 flk | 1 unknown maize gene | 1 |
| Hbr43 flk | None | >10 |
| Hbr45 flk | 1 unknown maize gene | 1 |
| Hbr46 flk | Maize 316-bp insertion element; 2 unknown maize genes | >10 |
| Hbr47 flk | Maize transposable element Bg sequence; 1 unknown maize gene | ND |
| Hbr48 flk | Similar to Arabidopsis light repressible receptor protein kinase; putative Ser/Thr protein kinase [Arabidopsis thaliana] | 1 |
| Hbr50 flk | None | 1 |
| Hbr51 flk | None | ND |
| Hbr54 flk | Maize 22-kDa alpha zein gene cluster; maize stripe virus noncapsid protein (NCP); nonstructural protein (NS4) genes; TA di-repeat | ND |
| Hbr56 flk | None | ND |
| Hbr58 flk | F19C22-T7 IGF Arabidopsis thaliana genomic clone F19C22 | ND |
| Hbr61 flk | 1 unknown maize gene | ND |
| Hbr62 flk | None | >10 |
| Hbr65 flk | Maize stripe virus noncapsid protein (NCP); nonstructural protein (NS4) genes; 1 unknown maize gene | 1 |
| Hbr68 flk | Maize DNA for tbp1 gene; Sorghum bicolor ADP-glucose pyrophosphorylase subunit SH2; Nbxb0004bB09r CUGI Rice BAC Library Oryza sativa genomic clone | ND |

*ND = not determined

PHI sequences found to have similarity to a Hbr-flanking sequence were then compared at the nucleotide level to the GenBank public database using BlastN 2.0. If a sequence residing in GenBank matched a PHI EST sequence with a score of at least 150 with P(N)<0.01, the gene name was associated with the PHI EST sequence. These gene names are reported in Table 2 under the column labeled Match. If additional PHI ESTs were found to have significantly similar nucleotide segments to a Hbr-flanking sequence, the associated GenBank names were included in Table 2. In the case of a PHI EST not having significant homology to a GenBank entry, a classification of 'Unknown' is given.

Analysis of Genomic Polymorphism Associated with Hbr Elements

The extent of Hbr polymorphism was investigated by comparing ten of the Hbr-containing loci previously isolated from strain GH94-1062 with the corresponding loci in the five teosinte strains and the eight maize inbred lines. The availability of the sequences of the Hbr elements and flanking regions of these loci facilitated the design of primers that were used in conjunction with a PCR assay to amplify orthologous loci in these strains.

Orthologous loci in these strains were PCR amplified using the primers (SEQ ID NOs:3–22) in Table 1. Polymorphism was detected at each locus when the products were visualized on agarose gels and stained with ethidium bromide. In almost all of the cases examined, the fragments detected differed in size by an amount that coincided with the length of the Hbr element, suggesting that the element was absent from the smaller fragments. To confirm this finding, all products were transferred to membranes and probed with Hbr-hm1. In all but one instance the smaller products did not hybridize with the Hbr-hm1 probe. Similarly, in all but one instance, the larger products hybridized with the element. All lanes hybridized with probes derived from the sequences flanking the corresponding Hbr elements, verifying that the orthologous locus had been amplified in each reaction.

Hbr Inserts Preferentially into Genic Regions

Previous studies have demonstrated that MITE elements are associated with hundreds of plant genes. However, the question of whether MITEs had a preference for insertion sites in genic regions could not be addressed since elements in these studies were identified following searches of gene-rich databases. In contrast, the Hbr elements isolated in this study provide an opportunity to address this question in an unbiased manner since they where chosen at random from a genomic library.

Two methodologies were used to characterize the Hbr insertion sites. First, target site copy number was estimated by probing Southern blots containing maize genomic DNA with labeled DNA isolated from the regions flanking 24 of the sequenced Hbr-containing fragments from GH94-1062. The 24 probes varied in length from 150 bp to 400 bp with most around 300 bp. Twelve probes hybridized with one to two bands, five probes detected-three to ten bands, and seven probes detected multiple (more than ten) bands or smear hybridization signals. Given that up to 80% of the maize genome has been estimated to be middle to highly repeated DNA, these results indicate a preference for insertion into low copy regions of the genome.

The second methodology involved the use of the flanking DNA sequences as queries of both the public and private (Pioneer and Dupont) databases of plant genes and maize ESTs. Thirty six Hbr-flanking sequences were used as queries to search the Pioneer EST/gene database (Pioneer Cornseq) at the nucleotide level. Twenty were found to match at least one of the maize EST/gene sequences at a significance level of P(N)<0.01 and a score of at least 200 (Table 2). Therefore, about 55% (20/36) of the Hbr elements analyzed to date may have inserted in or near sequences that show significant similarity to known genes or expressed regions of plant genomes. Of these 20, only four query sequences (Hbr10/Hbr68 and Hbr54/Hbr65) yielded redundant results. Sequences flanking Hbr10 and Hbr68 strongly matched the same region of the maize genome roughly 800 bp upstream the tbp1 gene's transcriptional start site (Goddemeier et al., GenBank Accession X90652), however they are not 100% identical. Also noteworthy is that these maize sequences have strong homology to ADP-glucose pyrophosphorylase subunit (SH2) from sorghum (Chen,M., SanMiguel et al., GenBank Accession AF010283) which had previously been found to contain several Tourist elements. However the sorghum SH2 region which shows similarity to the maize Hbr insertion sites was not reported to contain any such elements. It appears that we do not pick up similarity to maize SH2 with Hbr10 and Hbr68 flanking sequence because the available sequences for maize SH2 are cDNA and not genomic.

EXAMPLE 2

Generation of a DNA Fingerprint using a Detectable Label

This Example Deomonstrates the use of MITEs to Produce a DNA Fingerprint

Plant Material and Genomic DNA extraction. Two maize recombinant inbred populations were used in this study. One comprised 37 recombinant inbred lines (RILs) that were derived from a cross between inbreds CO159 and Tx303 (n=37) (Burr et al., Genetics, 118:519–526 (1988). A larger population of 100 RILs was derived from a cross between inbreds B73 X Mo17 (Austin et al., Theor. Appl. Genet, 92:817–826 (1996)). Hbr-transformed and non-transformed rice strains (O. sativa) were obtained from C. Fauquet (Scripps Research Institute).

DNA was extracted from leaf tissue of single plants as described (Ferreira et al., Embrapa-Cenargen Documento 20, Lumma Consultoria Projetos e Informantica, Brasilia, Brasil, 125–130 (1995)). The crude nucleic acid precipitates were suspended in TE (10 mM Tris-HCl, pH 8.0; 1 mM EDTA), incubated with RNAse at 37° C. for 1 hour, and quantified by fluorescence with a plate reader (Perkin-Elmer, model LS50B).

Hbr Transposon Display

DNA restriction and ligation (R/L) of adaptors. Initially, total genomic DNA (500 ng for maize and 50 ng for rice) was digested in a 40.0 μl cocktail containing 2 U MseI or 2 U BfaI (New England Biolab) (see Table 4 for list of materials and reagents used in Example 2), 5 mM Dithiothreitol (DTT), 5 μg of Bovine serum albumin (BSA) and 1×One-phor-all buffer plus. This reaction was incubated at 33° C. for 3 hours.

MseI adaptors (Table 3) were ligated to the digested DNA by addition of 10.0 μl of a mix containing 1×One-phor-all buffer, 1.2 mM of Adenosine 5'-triphosphate (ATP) (Sigma), 5 mM DTT, 5 μg of BSA (1 mg/ml), 50 pmol Mse adaptors, and 1 Weiss unit of T4 DNA ligase and incubating for 3 hours at 37° C. Since MseI and BfaI generate identical 3' overhangs, the same adaptors were used in both ligations. An aliquot of the R/L reactions was visualized on a 0.8% agarose gel. The R/L reactions were then diluted 4× with 0.1×TE (1×TE is (Tris 10 mM, EDTA 1 mM, pH 7.5.

TABLE 3

Sequence of adaptor and primers.

| Reaction | Primer identification | Sequence |
| --- | --- | --- |
| Digestion and ligation | MseI Adaptor | 5'- GACGATGAGTCCTGAG<br>3'- TACTCAGGACTCAT<br>(SEQ ID NO:23) |
| Pre-amplification | HbrInt5-E | 5' - GATTCTCCCCACAGCCAGATTC<br>(SEQ ID NO:24) |
| | MseI+0 | 5' - GACGATGAGTCCTGAGTAA<br>(SEQ ID NO:25) |
| | BfaI | 5'-GACGATGAGTCCTGAGTAG<br>(SEQ ID NO:39) |
| Selective amplification | HbrInt5-F | 5' -AGCCAGATTTTCAGAAAAGCTG<br>(SEQ ID NO:30) |
| | Mse+N | 5' - GACGATGAGTCCTGAGTAAN<br>(SEQ ID NO:31), where N can be any nucleotide |
| | BfaI+N | 5'-GACGATGAGTCCTGAGTAGN<br>(SEQ ID NO:40), where N can be any nucleotide |

TABLE 4

Materials and Reagents used.

| Reagent/Equipment | Company | Catalog number |
| --- | --- | --- |
| [-$^{33}$P] ATP | NEN Life Science Products, Inc. | NEG-602H |
| 30–330 AFLP DNA ladder | Gibco/BRL | 10832-012 |
| 40% Acrylamide-Bis 19:1 Solution | BIORAD | 161-0144 |
| A/E glass fiber filter | GelmanSciences | 61630 |
| Ammonium persulfate | Amresco | 7727-54-0 |
| AmpliTaq DNA polymerase | Perkin-Elmer | N808-0161 |
| ATP (Adenosine 5'-Triphosphate) | Sigma | A-7699 |
| Biomax MR-1 Film | Kodak | 8715187 |
| Blue dextran | Sigma | D-5751 |
| Boric acid | BIORAD | 161-0750 |
| dNTPs | Gibco/BRL | 18427-013 |
| DTT (Dithiothreitol) | Sigma | D-9779 |
| EDTA | Sigma | E-5134 |
| Formamide | Amresco | 75-12-7 |
| Genescan 500 XL [TAMRA] | Applied Biosystem/Perkin-Elmer | 403040 |
| Mixed bed resin | Sigma | M-8032 |
| MseI enzyme | New England Biolab | 525S |

TABLE 4-continued

Materials and Reagents used.

| Reagent/Equipment | Company | Catalog number |
|---|---|---|
| One-phor-all buffer plus | AmershamPharmacia BIotech | 27-0901 |
| PCR nucleotide mix | Promega | C1145 |
| T4 DNA ligase | Gibco/BRL | 15224-025 |
| T4 DNA ligase | New England Biolab | 202S |
| T4 polynucleotide kinase | Gibco/BRL | 18004-10 |
| Taq DNA polymerase | Promega | M1665 |
| TEMED | Amresco | 110-18-9 |
| Tris | Sigma | T-8524 |
| Urea | BIORAD | 161-0730 |
| Xylene Cyanole FF | Sigma | X-4126 |
| Bromophenol blue | Sigma | B-5525 |
| Whatman filter paper | Whatman | 09-806A |

Pre-selective (PA) reactions. The PA reactions were done with a primer complementary to the Mse adaptors (MseI+0; SEQ ID NO:25) or BfaI; SEQ ID NO:39) and another primer complementary to the Hbr element sequence (HbrInt5-E) (SEQ ID NO:24) (see FIG. 4). For experiments done in radioactive format, reactions were performed in 50 μl containing 5 1 of the diluted restriction/ligation reactions, 12 pmol of each primer, 1×GeneAmp PCR buffer II (Perkin-Elmer/ABI), 0.2 mM dNTPs, 2.5 mM MgCl$_2$ and 1 U AmpliTaq DNA polymerase (Perkin-Elmer/ABI). PCRs to be assayed in fluorescent format were done in 20 μl containing 3 μl of the diluted reactions, 8 pmol of each primer, 1×GeneAmp PCR buffer II, 0.2 mM dNTPs, 1.5 mM MgCl$_2$ and 0.4 U AmpliTaq. These and subsequent reactions were carried out with either a Robocycler Gradient Temperature Cycler (Stratagene), a Thermal Cycler Perkin-Elmer 480, or a PTC-100 Programmable Thermal Controller (MJ Research). The temperature cycling parameters were as follows: 72° C./2 min; 94° C./3 min; 24 cycles of 94° C./30 sec, 59° C./30 sec and 72° C./1 min; and a final cycle of 72° C./5 min. After visualizing aliquots of each PCR on 1.2% agarose gels stained with ethidium bromide, the remaining volumes were diluted twenty-fold with 0.1×TE.

Selective amplifications. Selective amplifications for radioactive detection were performed in 20 μl containing 5 μl of the diluted pre-selective amplifications, 8 pmol of selective primer Mse I+N (SEQ ID NO:31) or BfaI+N (SEQ ID NO:40), 1.25 pmol $^{33}$P-labeled HbrInt5-F (SEQ ID NO:30), 1×GeneAmp PCR buffer II, 0.2 mM dNTPs, 2.5 mM MgCl$_2$ and 0.4 U AmpliTaq DNA polymerase. For the fluorescent assay, PCRs were as above except that both Mse I+N and Bfa I+N primers (4 pmol) were used in combination with the HbrInt5-F primer (30 ng) labeled with 6-FAM (Perkin-Elmer/ABI) as suggested by the manufacturer, and the MgCl$_2$ concentration was reduced to 1.5 mM. Temperature cycling employed a "touchdown" protocol: 94° C./5 min; followed by 94° C./30 sec, 70° C./30 sec, and 72° C./1 min. In subsequent cycles, the annealing temperature was reduced from 69° C. to 61° C. in 1° C. increments each cycle. Twenty-seven cycles were performed at the 61° C. annealing temperature, followed by a final cycle of 72° C./5 min.

Primer labeling. To produce enough labeled HbrInt5-F primer for 20 PCR reactions, 2.5 μl of the primer (10 pmol/l) was labeled with 5 μl of [$^{33}$P] ATP (10 Ci/l), 1.0 μl of T4 polynucleotide kinase (10 U/l), 1.25 μl of 10×One-phor-all buffer and 2.75 μl of water. The reaction was incubated for 30 minutes at 37° C., for 10 minutes at 70° C., centrifuged briefly, and used directly for PCR.

Labeling of 30–330 bp AFLP DNA ladder. Two μl of 30–330 base pair AFLP DNA ladder, 1.0 μl of Exchange Reaction Buffer (250 mM imidazole [pH 6.4], 60 mM MgCl$_2$, 5 mM 2-Mercaptoethanol, 350 μM ADP) (Gibco/BRL), 1.0 μl of [$^{-33}$P] ATP (10 Ci/l), and 1.0 μl of T4 polynucleotide kinase (10 U/i) were added to a 0.5 ml tube on ice. After mixing thoroughly and centrifuging briefly, the mixture was incubated for 10 minutes at 37° C. The reaction was stopped by heating the tube for 15 minutes at 65° C. An equal volume of TE buffer, and 25 μl of loading denaturing buffer was added. TE buffer is 10 mM Tris base, 1 mM EDTA at pH 7.5, final pH adjusted to pH 8.0. Loading denaturing buffer was made by combining 10 ml formamide, 10 mg xylene cyanole FF, 10 mg bromophenol blue, and 200 μl of 10 mM EDTA.

Gel Preparation

6% denaturing acrylamide-bisacrylamide (19:1) (7.5M urea) gels for radioactive label. Twenty-five ml of water plus 12.0 ml of 40% Acrylamide/Bisacrylamide (19:1) solution were added to 36 grams of urea in a 250 ml Erlenmeyer flask and stirred 5 minutes. Subsequently, 500 mg of mix bed resin was added and stirred for 5 more minutes. The solution was then filtered in a 0.2 micron A/E glass fiber filter and degassed for 5 minutes. Eight mls of 10×TBE buffer was added, and then water up to 80.0 ml. TBE (10×) is 890 mM Tris base, 890 mM Boric acid, and 20 mM EDTA. Immediately before pouring the gel, 300.0 μl of 10% ammonium persulfate and 56.0 μl TEMED were added to the gel solution. The gel was allowed to polymerize for 2 hours and pre-run at constant current (35 mA) until it reached 48° C.

For fluorescent label. Twenty ml of water plus 6.3 ml of 40% Acrylamide/Bisacrylamide (19:1) solution were added to 18 gram of urea (BIORAD) in a 250 ml Erlenmeyer and stirred 5 minutes. Subsequently, 500 mg of mix bed resin (Sigma) was added and stirred for 5 more minutes. The solution was then filtered in a 0.2 micron glass fiber filter (GelmanSciences) and degassed for 5 minutes. Five milliliters of 10×TBE buffer (10×TBE is 890 mM Tris, 890 mM borate, 20 mM EDTA) and water up to 50.0 ml. Immediately before pouring the gel, 250.0 μl of 10% ammonium persulfate (Amresco) and 35.0 μl TEMED (Amresco) were added to the gel solution. The gel was let to polymerize for 2 hours and pre-run at constant voltage (1000V) until it reached 51° C.

Sample Preparation

Radioactive label. Initially 20.0 μl of loading denaturing buffer was added to the PCR reactions. The samples were then denatured at 95° C. for 5 minutes, placed on ice, and 3.0 μl of the mixture was immediately loaded on the gels in 1×TBE buffer (89 mM Tris, 89 mM borate, 2 mM EDTA). The size standard, the 30–330 bp AFLP DNA ladder, was also denatured and 2.0 μl of it was loaded on the gel.

Fluorescent label. Samples containing 0.3 μl of the PCR products, 0.1 μl GeneScan 500×L [TAMRA] internal lane size standard (Applied Biosystems/Perkin-Elmer) and 1.6 μl of loading buffer (4 parts deionized formamide: 1 part blue dextran dye) were denatured at 95° C. for 5 minutes, placed on ice, and 0.8 μl of the mixture was immediately loaded on 5% denaturing (6M urea) acrylamide-bisacrylamide (19:1) gels in 1×TBE buffer.

Electrophoresis

Radioactive label. Samples were electrophoresed (35 mA constant) for 2 hours. The gel was then transferred to a Whatman filter paper, dried at 60° C. for 45 minutes and exposed to an X-ray film (Biomax MR-1) for at least one day.

Fluorescent label. Samples were electrophoresed (3000V) for 3 hours at 51° C. in 1×TBE buffer, on an automated DNA sequencer (ABI Prism Model 377) according to the manufacturer's suggestions.

Recovery of Gel Bands. Thirty-eight DNA fragments were excised from radioactive gels, eluted in buffer (0.5 M NH40ac, 10 mM MgCl2, 0.1% SDS, 1 mM EDTA, pH 8.0), precipitated with ethanol and suspended in 10 µl TE. Fragments were amplified in 50 µl containing 5 µl DNA, 12 pmol of each primer (Mse I+N and HbrInt5-F), 1×GeneAmp PCR buffer II, 0.2 mM dNTPs, 2.5 mM $MgCl_2$ and 1 U of AmpliTaq DNA polymerase. PCRs were performed using the "touchdown" cycling protocol described above. Reactions were resolved on a 1% agarose gel and fragments were excised and purified following the QIAquick gel extraction kit protocol (QIAGEN). Cloning was done with a commercial kit (TA cloning kit, INVITROGEN) and DNA sequence data were obtained using fluorescent dye terminator chemistry and automated DNA sequencers (Model 373A, Perkin-Elmer/ABI).

Mapping of Hbr-insertion Sites. All mapping data were collected in fluorescent format. Electropherograms were analyzed and DNA fragments sized using GeneScan v. 2.1 software (Perkin-Elmer/ABI). Peak scoring was verified for each DNA sample and a fragment presence/absence matrix was generated for both mapping populations using Genotyper v. 2.5 (Perkin-Elmer/ABI). The frequency of non-parental bands was calculated by dividing the absolute number of non-parental fragments by the total number of bands scored in all progeny. Non-parental bands included both fragments scored in either parent but absent in the progeny and bands scored in the progeny but absent in either parent.

Linkage analysis of Hbr markers was performed with Mapmaker v. 3.0 (Lander et al., *Genomics*, 1:1 741–181 (1987)). To include a locus in a linkage group, a minimum LOD threshold of 3.0 and a recombination fraction (rf) of 0.40 were used. Because the B73XMo17 recombinant inbred population was constructed by four rounds of intermating prior to establishment of selfed lines, rf values calculated by MapMaker were corrected as described (Liu et al., *Genetics*, 142:247–258 (1996)). Three-point analyses followed by multipoint analyses were done to determine the putative order between the loci. This analysis produced 19 linkage groups that were placed into the standard 10 linkage groups by comparisons to published maps using the Maze Genome Database, MaizeDB avaiable at the internet address.

A chi-square test for goodness of fit was used to determine if the Hbr markers were evenly distributed among the 10 maize chromosomes. The expected number of markers per chromosome was estimated by multiplying the total number of markers observed by the proportion of the total genetic length of the map (cM) represented by each chromosome.

Results

Mapping strategy. Transposon display was developed with alternative goals in mind. The first was as a rapid screen for newly transposed MITEs. The second was to rapidly determine the map positions of hundreds of Hbr elements and, in the process, develop a new class of molecular marker. Recombinant inbred mapping populations were chosen for Hbr-transposon display since high frequencies of non-parental bands in the recombinant inbred lines (RILs) might indicate new transpositions. However, if non-parental bands were rare, then polymorphic parental bands could be mapped following segregation analysis in the RILs.

PCR products are anchored in Hbr elements. Hbr-display was initially tested using a small mapping population derived from a cross between maize inbreds CO159 and Tx303. To confirm that the fragments resulting from transposon display were anchored in Hbr elements, 38 bands were recovered, re-amplified, cloned and sequenced. Bands were chosen from each of the four MseI selective amplifications (HbrInt5-F/MseI+A, G, C, and T) and included 30 polymorphic fragments and four pairs of co-migrating (monomorphic) parental bands.

All 38 clones contained the Hbr TIR sequence adjacent to the Hbr Int5-F primer, thus confirming that all were anchored in Hbr elements. The DNA sequences of three co-migrating fragments from CO159, each amplified with a different selective primer set (HbrInt5-F/MseI+A, G or T), had unique flanking sequences and contained the appropriate 3' selective base. These data demonstrate that the addition of specific nucleotides to the 3' end of the MseI primer resulted in the amplification of different Hbr-containing fragment sets. In contrast, the DNA sequences were identical for three of four monomorphic fragment pairs assayed. The fourth pair differed both in sequence and length (by one base pair) indicating that co-migrating fragments had not been resolved and isolated.

Genomic distribution of Hbr-anchored fragments. To determine the genomic distribution of Hbr elements and to assess the utility of transposon display fragments as a new molecular marker class, display fragments were mapped in a much larger population of 100 RILs derived from a cross between the maize inbreds B73 and Mo17 (Austin et al., *Theor. Appl. Genet.*, 92:817–826 (1996)). This analysis was done using semi-automated, fluorescence-based detection since the sensitivity, band resolution, and sizing precision were judged to be superior to the radioactive format.

Figure 5:
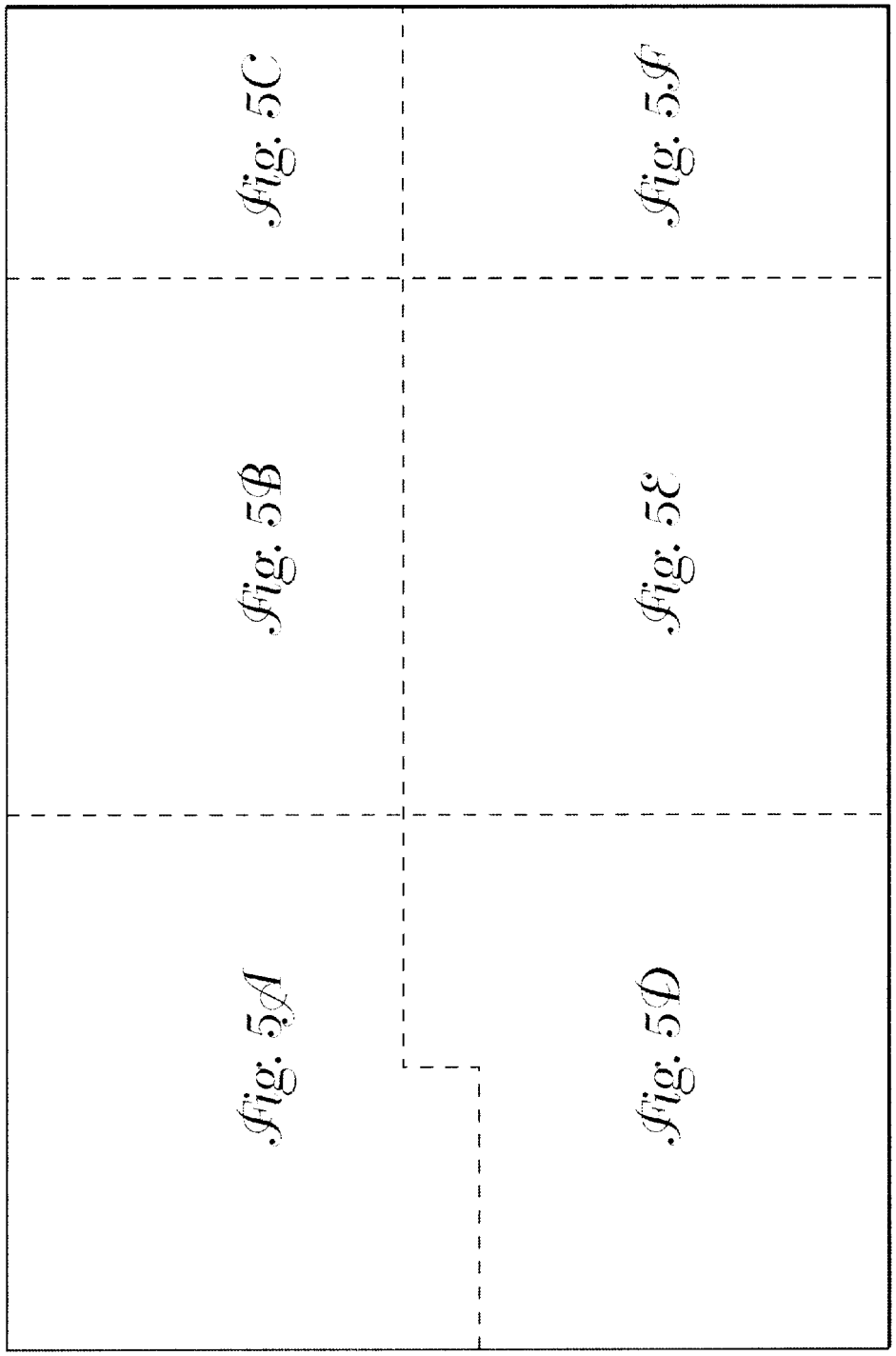
FIG. 5. Genetic map of maize with Hbr and RFLP markers. Two hundred and thirteen Hbr markers were assigned to the ten maize chromosomes using a previously established map of 282 RFLP markers (only a fraction is shown). The total genetic length of the map was 1,092 cM. Hbr-markers are marked with a 0 (from B73) and a † (from Mo17). Hbr-markers in parentheses were completely linked (no recombination) to other Hbr-markers. Those marked with an asterisk were separated by less than 1.2 cM. Markers showing segregation distortion are indicated by a double-plus sign. For each Hbr-marker, the following information has been provided: DNA element and respective family from which the marker derived (mHbr=MiteHeartbreaker); the restriction enzyme used (M and B for fragments generated by MseI and BfaI, respectively); the selective base employed (A, C, G or T) and the size of the fragment in base pairs. Numbers to the left of each chromosome represent distances (cM) and recombination fractions, respectively.
Figure 5A:
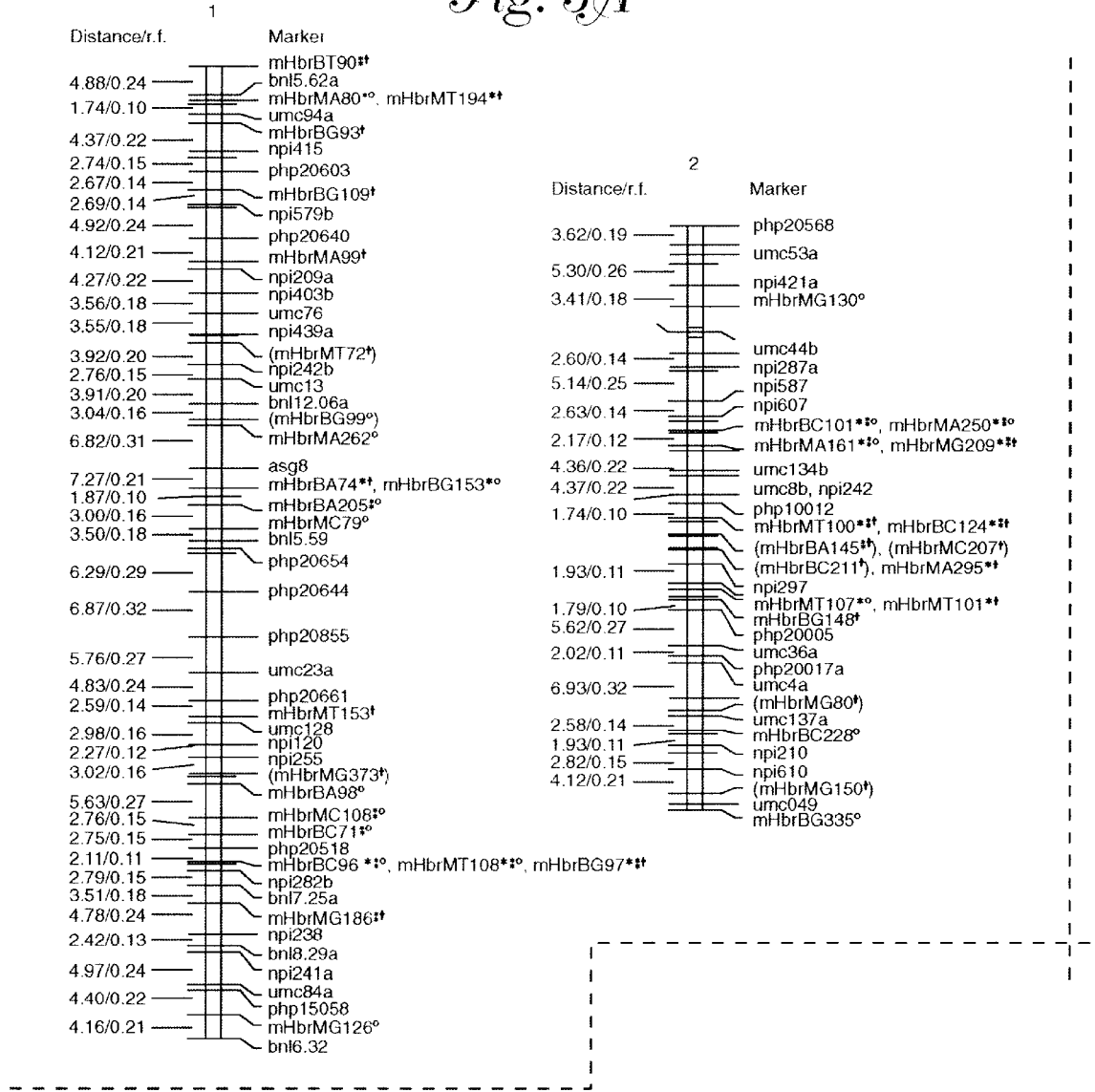
Figure 5B:
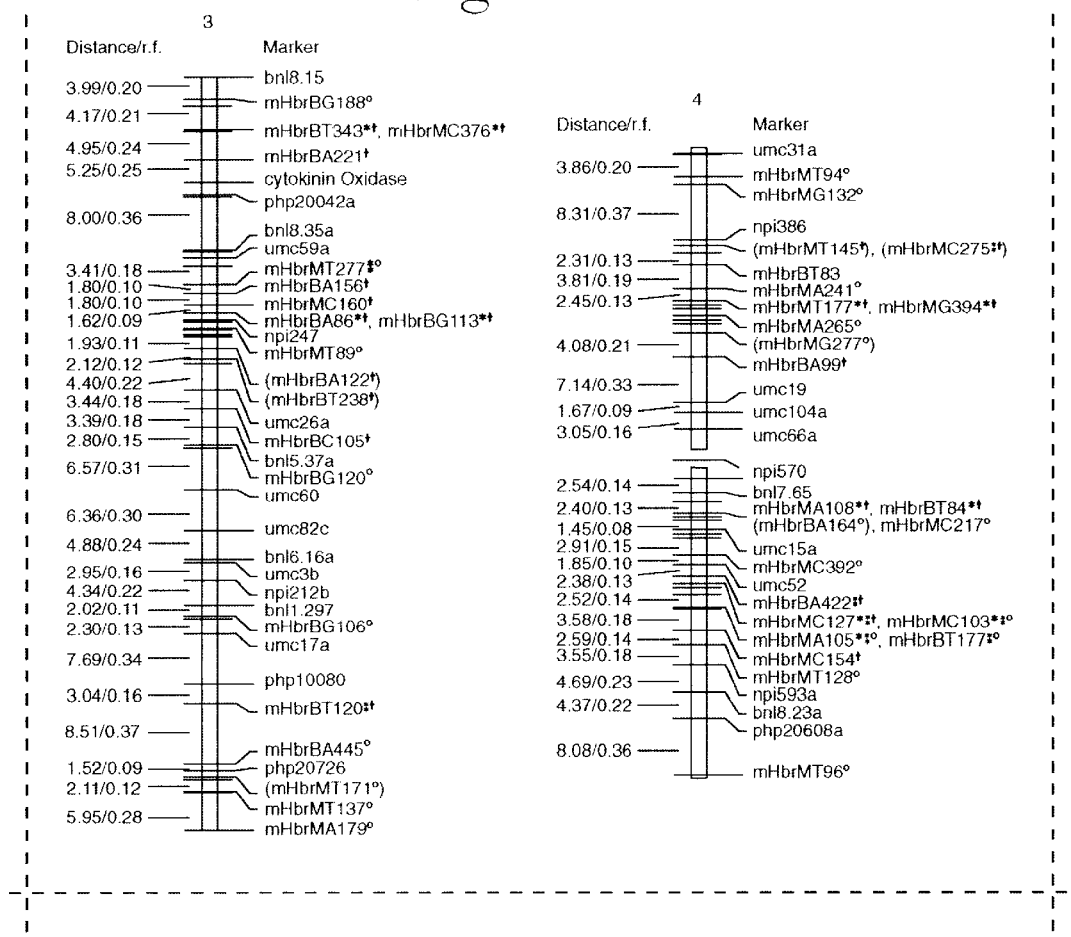
Figure 5C:
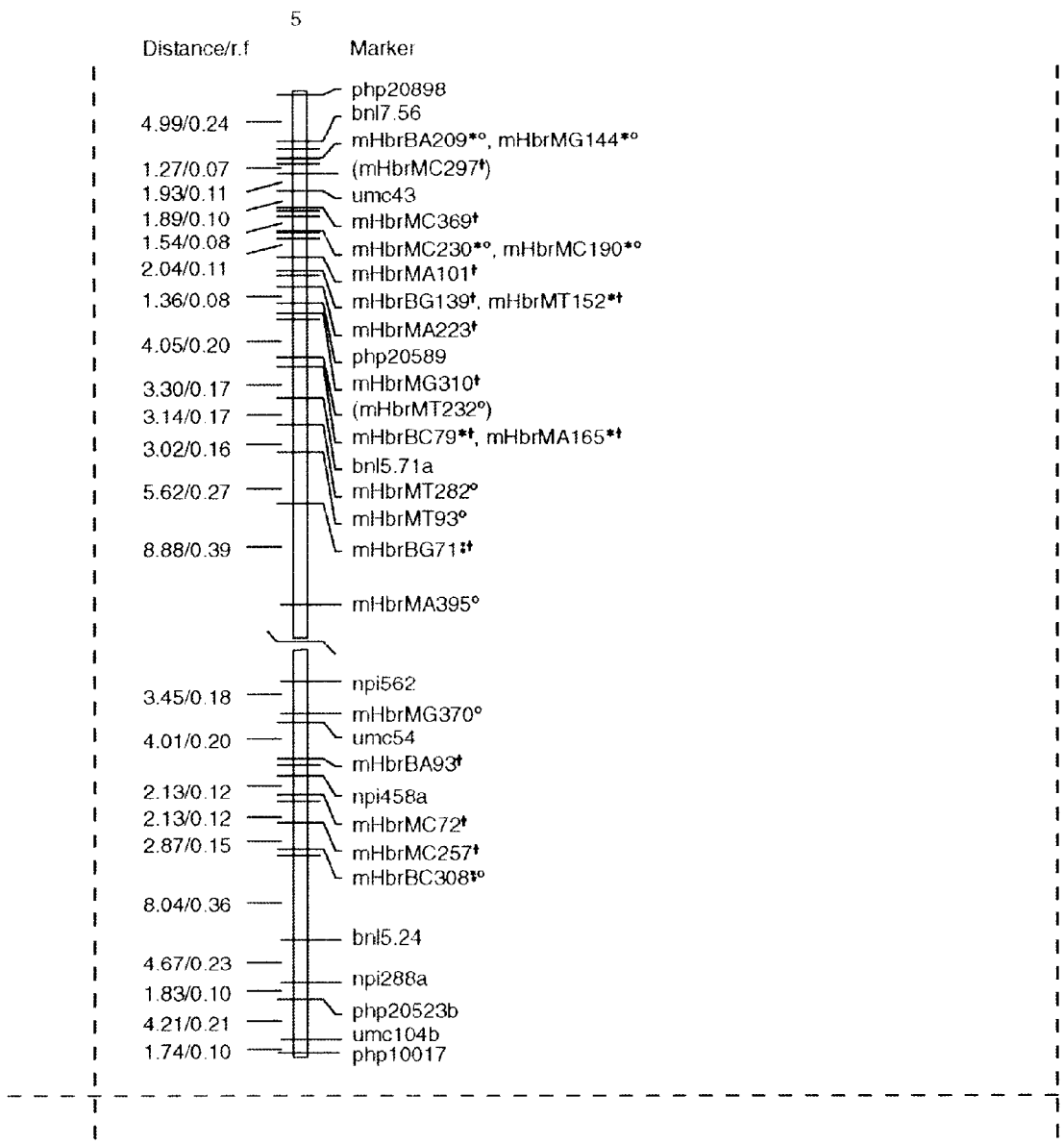
Figure 5D:
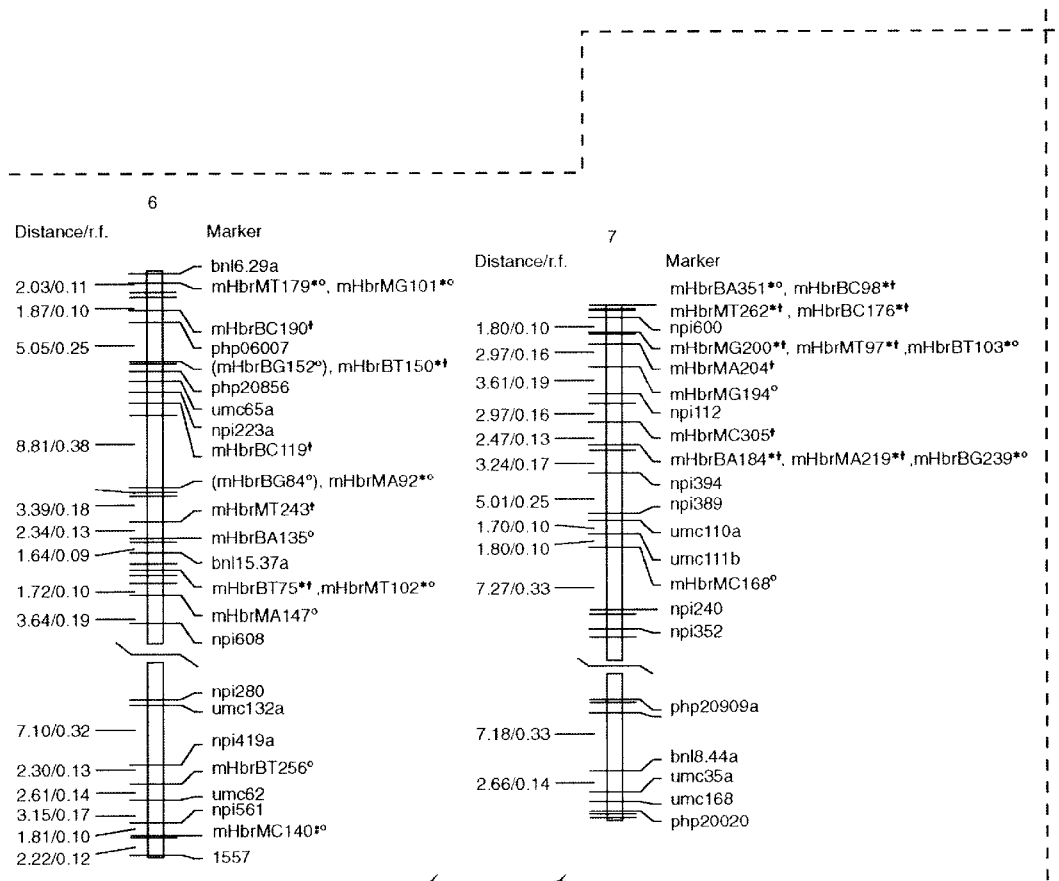
Figure 5E:
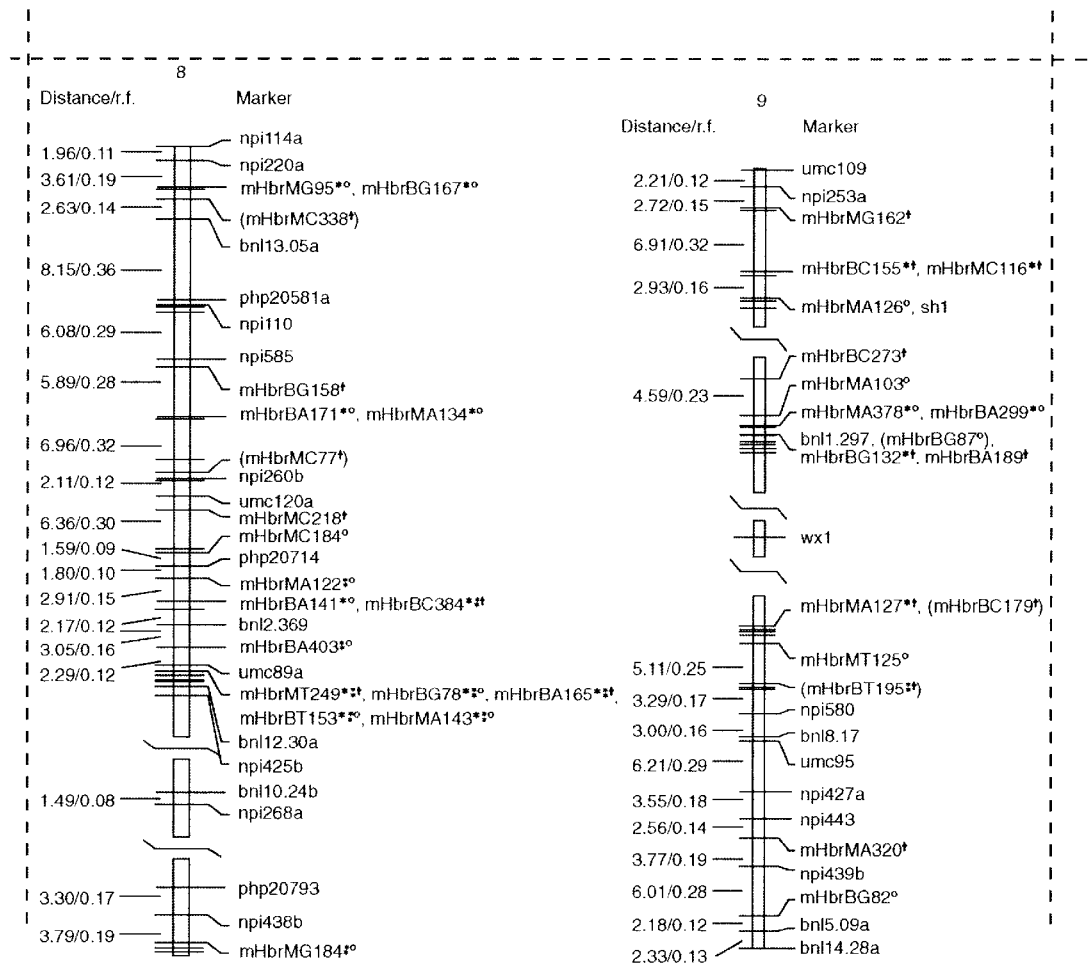
Figure 5F:
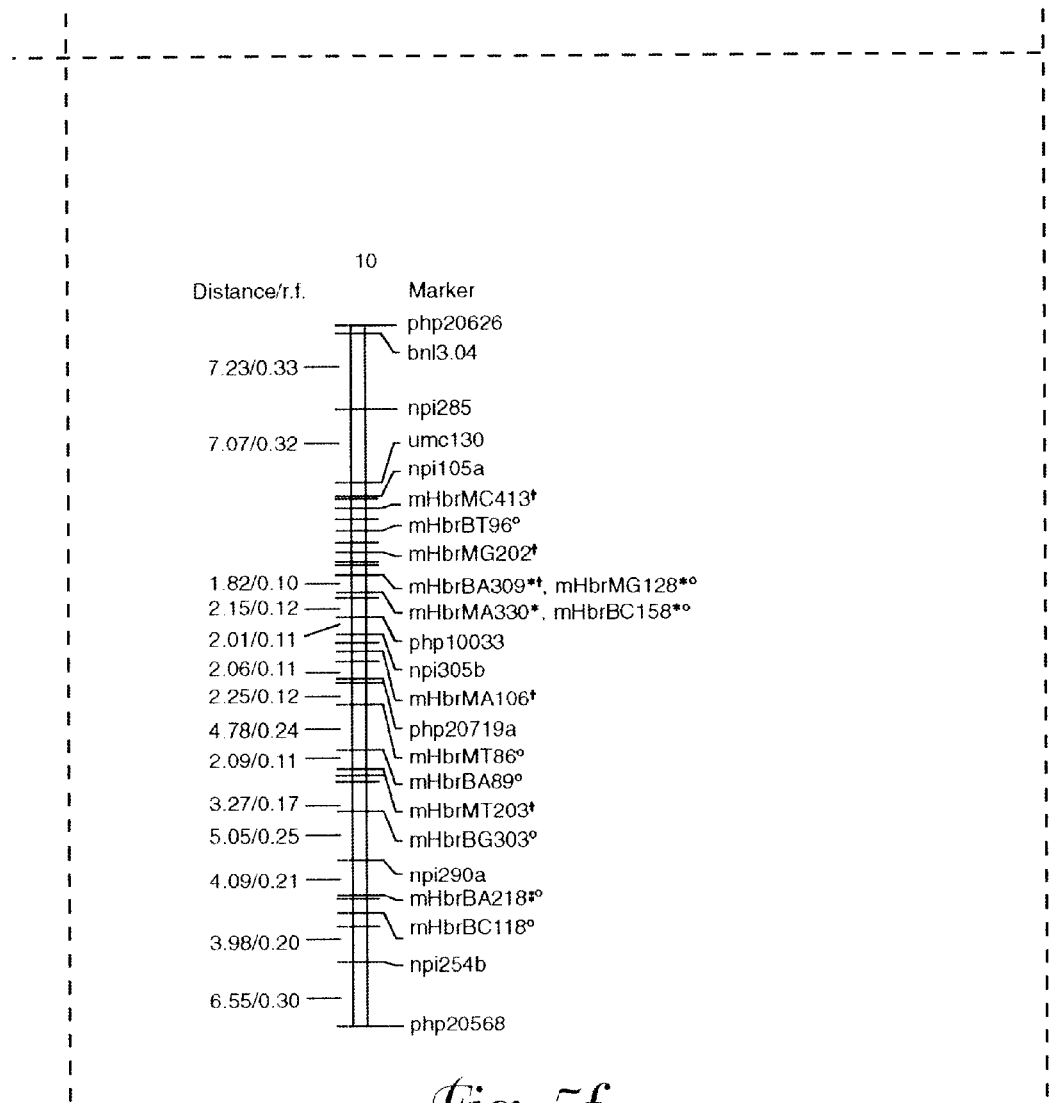

A total of 418 fragments (65 to 450 base pairs) from eight primer combinations (223 from Hbr5-F/Mse I+N and 195 from Hbr5-F/Bfa I+N) were unambiguously scored in the parental lines. The number of fragments amplified and the polymorphisms detected for each primer combination are summarized in Table 5. Among all primer combinations, the number of amplified fragments ranged from 42 (HbrInt5-F/BfaI+C) to 77 (HbrInt5-F/MseI+A). Overall, 252 of the 418 fragments, or 60.3%, were polymorphic and could be assigned to specific maize chromosomes by determining linkage relationships to 282 previously mapped RFLP markers (Lee et al., Abstract No. P268, Plant & Animal Genome VII Conference (January, 1999)). Of these 252 polymorphic markers, 213 (111 from Mo17 and 102 from B73) were assigned to chromosomes (FIG. 5). These will be referred to as "Hbr markers". Results from $\chi^2$ tests showed that the Hbr markers were evenly distributed in the maize genome ($\chi^2$2.5, p<0.01). When considered separately, both the BfaI ($\chi^2$=4.8, p<0.01) and MseI ($\chi^2$=6.3, p<0.01) markers were also evenly distributed. The Hbr markers, as a whole, mapped with an average LOD score of 43.6. The LOD scores for individual markers were greater than 8.0 except for one marker (mHbrMT96) that mapped to the telomeric region of chromosome 4 (LOD=3.75).

TABLE 5

Polymorphism detected in the B73 × Mo17 mapping population

| Primer/enzyme combination | Number of amplified fragments | | | % polymorphic |
|---|---|---|---|---|
| | Monomorphic | Polymorphic | Total | |
| Hbr – BfaI + A | 26 | 38 | 64 | 59.4 |
| Hbr – BfaI + C | 16 | 26 | 42 | 61.9 |
| Hbr – BfaI + G | 16 | 27 | 43 | 62.8 |
| Hbr – BfaI + T | 23 | 23 | 46 | 50.0 |
| Total | 81 | 114 | 195 | 58.5 |
| Hbr – MseI + A | 37 | 40 | 77 | 51.9 |
| Hbr – MseI + C | 13 | 33 | 46 | 71.7 |
| Hbr – MseI + G | 15 | 28 | 43 | 65.1 |
| Hbr – MseI + T | 20 | 37 | 57 | 64.9 |
| Total | 85 | 138 | 223 | 61.9 |

The total length of the genetic map was 1091.5 cM. Addition of Hbr markers to the maize RFLP map increased the genetic map length by 150 cM and reduced the overall distance between markers. Previously, there were 51 regions of the RFLP map where the recombination fraction was greater than 0.3. Inclusion of the Hbr markers reduced the number of these regions to 37.

No recombination was detected among 24 sets of markers (comprising a total of 50 markers or 23.5% of the 213 Hbr markers mapped) (FIG. 5). In most instances (79%), complete linkage was observed between a pair of MseI and BfaI markers. This result would be expected if these markers include the same Hbr insertion site. In a minority of cases, complete linkage involved either two BfaI markers (8.3%) or one MseI and two BfaI markers (12.5%). Since these markers were not sequenced, it is not known whether linkage in these cases was due to the same Hbr insertion or to tightly linked elements.

Segregation ratios that departed from the Mendelian expectation of 1:1 (p<0.05) were detected for 49 Hbr markers (19.5%; 26 in Mo17, 23 in B73). Thirty-nine distorted markers were mapped (FIG. 5). In general, these markers were not evenly distributed across all maize chromosomes, but clustered on chromosomes 1, 2, 4, and 8. Finally, 39 Hbr markers (15.5%) were not be mapped either because of low LOD scores (<3) or because linkage to the framework RFLP markers was not detected.

To determine whether polymorphic bands that co-migrated in the two mapping populations also co-mapped, the map positions of co-migrating Hbr markers that were polymorphic in both mapping populations were compared. For this experiment, markers were mapped from only the two primer combinations (Hbr5-F/Mse I+C and Hbr5-F/Mse I+G) that yielded the highest number of polymorphic fragments in the B73×Mo17 mapping population (Table 5). Fourteen Hbr markers were common between the two mapping populations. The chromosomal locations matched for 13 markers (93%), while one mapped to a different location.

Non-parental inheritance. TD bands present in one or more progeny but absent in both parental inbreds or monomorphic between parents but missing in the progeny were defined as displaying non-parental inheritance. Seven RILs from the B73×Mo17 mapping population yielded a large number of markers showing non-parental inheritance for almost every primer pair combination tested. These lines also showed excessive non-parental bands when analyzed for the segregation of either RFLP or SSR markers, indicating that outcrossing probably occurred at some point during their development. If the aberrant lines are not considered, only thirty-one fragments out of 12,471 data points showed non-parental inheritance (0.25%) for all eight primer combinations tested.

In summary, these data demonstrate the development of a new class of molecular markers that should prove useful in a number of applications in maize and other organsims where MITE families exist. Hbr-markers are highly polymorphic among inbred lines, evenly distributed in the maize genome and, like AFLP markers, large numbers of markers can be easily generated and displayed in a semi-automated fashion. In contrast to AFLP markers, Hbr-markers advantageously insert into nonrepetitive genic regions. Thus, the technique is cost-effective, as limited numbers of primers (both generic and MITE-specific) are required. Although MITE primers are not universal like AFLP primers, primers for other MITEs can be identified by database searches. Finally, the data are extremely reproducible, both within and between mapping populations and fragments are easily recovered for possible conversion into sequence-based markers.

EXAMPLE 3

Amplification Conditions for other MITEs

The generation of a DNA fingerprint as described in the above Examples can be altered to amplify different MITEs.

Amplification of Hb2

The primers used in the pre-selective amplification reaction were SEQ ID NO:33 and SEQ ID NO:25. Temperature cycling was performed as follows: 72° C. for 2 minutes, followed by 94° C. for 3 minutes, followed by 24 cycles at 94° C. for 30 seconds, 56° C. for 30 seconds and 72° C. for 1 minute, and a final cycle at 72° C. for 5 minutes.

The primers used in the selective amplification reaction were SEQ ID NO:32 and SEQ ID NO:31. Amplification was done using a "touchdown" cycling protocol: one cycle at 94° C. for 3 minutes, followed by one cycle at 94° C. for 30 seconds, 66° C. for 30 seconds, and 72° C. for 1 minute. Subsequently, the annealing temperature was reduced from 72° C. to 60° C. in increments of 1° C. each cycle. Thirty additional cycles were then performed using 60° C. as the annealing temperature. Finally an extension of 72° C. for 5 minutes was employed.

Amplification of mPIF

The primers used in the pre-selective amplification reaction were SEQ ID NO:34 and SEQ ID NO:25. Temperature cycling was performed as follows: 72° C. for 2 minutes, followed by 94° C. for 3 minutes, followed by 24 cycles at 94° C. for 30 seconds, 56° C. for 30 seconds and 72° C. for 1 minute, and a final cycle at 72° C. for 5 minutes.

The primers used in the selective amplification reaction were 5' ASTWAGATTCCAATTCCTCAAAATGAA (SEQ ID NO:38) and SEQ ID NO:31. Amplification was done using a "touchdown" cycling protocol: one cycle at 94° C. for 5 minutes, followed by 2 cycles at 94° C. for 30 seconds, 65° C. for 45 seconds, and 72° C. for 1 minute, 2 cycles at 94° C. for 30 seconds, 64° C. for 45 seconds, and 72° C. for 1 minute, 2 cycles at 94° C. for 30 seconds, 63° C. for 45 seconds, and 72° C. for 1 minute, 2 cycles at 94° C. for 30 seconds, 62° C. for 45 seconds, and 72° C. for 1 minute, 2 cycles at 94° C. for 30 seconds, 61° C. for 45 seconds, and 72° C. for 1 minute, 2 cycles at 94° C. for 30 seconds, 60°

C. for 45 seconds, and 72° C. for 1 minute, and 2 cycles at 94° C. for 30 seconds, 59° C. for 45 seconds, and 72° C. for 1 minute, followed by 72° C. for 5 minutes.

Amplification of B2

The primers used in the pre-selective amplification reaction were SEQ ID NO:37 and SEQ ID NO:25. Temperature cycling was performed as follows: 72° C. for 2 minutes, followed by 94° C. for 3 minutes, followed by 24 cycles at 94° C. for 30 seconds, 58° C. for 30 seconds and 72° C. for 1 minute, and a final cycle at 72° C. for 5 minutes.

The primers used in the selective amplification reaction were SEQ ID NO:36 and SEQ ID NO:31. Amplification was done using one cycle at 94° C. for 3 minutes, followed by thirty cycles at 94° C. for 30 seconds, 59° C. for 30 seconds, and 72° C. for 1 minute. Finally an extension of 72° C. for 5 minutes was employed.

The complete disclosures of all patents, patent applications, publications, and nucleic acid and protein database entries, including for example GenBank accession numbers and EMBL accession numbers, that are cited herein are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

Sequence Listing Free Text

| | |
|---|---|
| SEQ ID NOs: 1–22 | Oligonucleotide primer |
| SEQ ID NOs: 23 | Adaptor oligonucleotide |
| SEQ ID NO: 24–25 | Oligonucleotide primer |
| SEQ ID NO: 30 | Oligonucleotide primer |
| SEQ ID NO: 31 | Oligonucleotide primer, where N can be any nucleotide |
| SEQ ID NO: 32–39 | Oligonucleotide primer |
| SEQ ID NO: 40 | Oligonucleotide primer, where N can be any nucleotide |

What is claimed is:

1. A method for producing a DNA fingerprint of an individual comprising:

providing a plurality of restriction fragments wherein the restriction fragments comprise an adaptor;

amplifying at least a portion of the restriction fragments with a primer pair, wherein the nucleotide sequence of one primer of the primer pair is complementary to a portion of a miniature inverted repeat transposable element that is a member of a miniature inverted repeat family, and wherein the other primer of the primer pair comprises at the 5' end a nucleotide sequence complementary to at least a portion of the adaptor; and resolving the amplified fragments to produce a DNA fingerprint.

2. The method of claim 1 wherein providing the plurality of restriction fragments comprising an adaptor comprises:

digesting DNA of the individual with a restriction endonuclease to result in a plurality of restriction fragments, wherein each restriction fragment has two ends; and ligating a double stranded adaptor to an end of the plurality of restriction fragments.

3. The method of claim 1 wherein at least about 70% of the miniature inverted repeat transposable elements of the miniature inverted repeat family are present in genic regions.

4. The method of claim 1 wherein the DNA is genomic DNA.

5. The method of claim 1 wherein the individual is a plant.

6. The method of claim 5 wherein the plant is selected from the group consisting of maize and teosinte.

7. The method of claim 6 wherein the plant is maize.

8. A method for producing a DNA fingerprint of a maize comprising:

providing a plurality of restriction fragments wherein the restriction fragments comprise an adaptor;

amplifying at least a portion of the restriction fragments with a primer pair, wherein the nucleotide sequence of one primer of the primer pair is complementary to a portion of a miniature inverted repeat transposable element that is a member of a miniature inverted repeat family, wherein the miniature inverted repeat transposable element has at least about 90% identity to SEQ ID NO:26, or the complement thereof, wherein the other primer of the primer pair comprises at the 5' end a nucleotide sequence complementary to at least a portion of the adaptor; and resolving the amplified fragments to produce a DNA fingerprint.

9. The method of claim 7 wherein the miniature inverted repeat transposable element has at least about 90% identity to SEQ ID NOs:28, or the complement thereof.

10. A method for producing a DNA fingerprint of a maize comprising:

providing a plurality of restriction fragments wherein the restriction fragments comprise an adaptor;

amplifying at least a portion of the restriction fragments with a primer pair, wherein the nucleotide sequence of one primer of the primer pair is complementary to a portion of a miniature inverted repeat transposable element that is a member of a miniature inverted repeat family, wherein the miniature inverted repeat transposable element has at least about 90% identity to SEQ ID NO:29, or the complement thereof, wherein the other primer of the primer pair comprises at the 5' end a nucleotide sequence complementary to at least a portion of the adaptor; and resolving the amplified fragments to produce a DNA fingerprint.

11. The method of claim 7 wherein the miniature inverted repeat transposable element has at least about 90% identity to SEQ ID NO:27, or the complement thereof.

12. The method of claim 1 wherein the amplified fragments are resolved by electrophoresis.

13. The method of claim 1 wherein one of the primers comprises a detectable label.

14. The method of claim 13 wherein the detectable label is selected from the group consisting of a radioactive label, a fluorescent label, a chemiluminescent label, and a combination thereof.

15. A method for detecting at least one polymorphism, the method comprising:
   producing a DNA fingerprint of a first individual and a DNA fingerprint of a second individual comprising;
      providing a plurality of restriction fragments from each individual, wherein the restriction fragments comprise an adaptor;
      amplifying at least a portion of the restriction fragments with a primer pair, wherein the nucleotide sequence of one primer of the primer pair is complementary to a portion of a miniature inverted repeat transposable element that is a member of a miniature inverted repeat family, and wherein the other primer of the primer pair comprises at the 5' end a nucleotide sequence complementary to at least a portion of the adaptor; and
      resolving the amplified fragments to produce a DNA fingerprint of each individual; and
   comparing the amplified fragments of the individuals to detect the presence or absence of at least one amplified fragment, wherein the presence or absence of at least one amplified fragment indicates the presence of at least one polymorphism.

16. The method of claim 15 wherein providing the plurality of restriction fragments comprising an adaptor comprises:
   digesting DNA of the individual with a restriction endonuclease to result in a plurality of restriction fragments, wherein each restriction fragment has two ends; and
   ligating a double stranded adaptor to an end of the plurality of restriction fragments.

17. The method of claim 15 further comprising repeating the producing and comparing steps with additional individuals.

18. The method of claim 15 wherein the first individual and second individual are members of a recombinant inbred mapping population.

19. The method of claim 15 wherein at least about 70% of the miniature inverted repeat transposable elements of the miniature inverted repeat family are present in genic regions.

20. The method of claim 15 wherein the DNA is genomic DNA.

21. The method of claim 15 wherein each individual is a plant.

22. The method of claim 21 wherein the plant is selected from the group consisting of maize and teosint.

23. The method of claim 22 wherein the plant is maize.

24. A method for detecting at least one polymorphism, the method comprising:
   producing a DNA fingerprint of a first maize and a DNA fingerprint of a second maize comprising;
      providing a plurality of restriction fragments from each maize wherein the restriction fragments comprise an adaptor;
      amplifying at least a portion of the restriction fragments with a primer pair, wherein the nucleotide sequence of one primer of the primer pair is complementary to a portion of a miniature inverted repeat transposable element that is a member of a miniature inverted repeat family wherein the miniature inverted repeat transposable element has at least about 90% identity to SEQ ID NO:26, or the complement thereof, and wherein the other primer of the primer pair comprises at the 5' end a nucleotide sequence complementary to at least a portion of the adaptor; and
      resolving the amplified fragments to produce a DNA fingerprint of each maize; and
   comparing the amplified fragments of the maize to detect the presence or absence of at least one amplified fragment, wherein the presence or absence of at least one amplified fragment indicates the presence of at least one polymorphism.

25. The method of claim 23 wherein the miniature inverter repeat transposable element has at least about 90% identity to SEQ ID NO:28, or the complement thereof.

26. A method for detecting at least one polymorphism, the method comprising:
   producing a DNA fingerprint of a first maize and a DNA fingerprint of a second maize comprising;
      providing a plurality of restriction fragments from each maize wherein the restriction fragments comprise an adaptor;
      amplifying at least a portion of the restriction fragments with a primer pair, wherein the nucleotide sequence of one primer of the primer pair is complementary to a portion of a miniature inverted repeat transposable element that is a member of a miniature inverted repeat family wherein the miniature inverted repeat transposable element has at least about 90% identity to SEQ ID NO:29, or the complement thereof, and wherein the other primer of the primer pair comprises at the 5' end a nucleotide sequence complementary to at least a portion of the adaptor; and
      resolving the amplified fragments to produce a DNA fingerprint of each maize; and
   comparing the amplified fragments of the maize to detect the presence or absence of at least one amplified fragment, wherein the presence or absence of at least one amplified fragment indicates the presence of at least one polymorphism.

27. The method of claim 23 wherein the miniature inverted repeat transposable element has at least about 90% identity to SEQ ID NO:27, or the complement thereof.

28. The method of claim 15 wherein the amplified fragments are resolved by gel electrophoresis.

29. The method of claim 15 wherein one of the primers comprises a detectable label.

30. The method of claim 29 wherein the detectable label is selected from the group consisting of radioactive label, a fluorescent label, a chemiluminescent label, and a combination thereof.

31. A method for correlating the presence of an amplified fragment to a phenotype, the method comprising:
   producing a DNA fingerprint of a first individual and of a second individual, wherein the first individual displays a phenotype and the second individual does not display the phenotype, wherein producing a DNA fingerprint comprises;
      providing a plurality of restriction fragments wherein the restriction fragments comprise an adaptor;
      amplifying at least a portion of the restriction fragments with a primer pair, wherein the nucleotide sequence of one primer of the primer pair is complementary to a portion of a miniature inverted repeat transposable element that is a member of a miniature inverted repeat family, and wherein the other primer of the primer pair comprises at the 5' end a nucleotide sequence complementary to at least a portion of adaptor; and resolving the amplified fragments to produce a DNA fingerprint; and comparing the amplified fragments of each individual to detect a difference between the amplified fragments of the first individual and the amplified fragments of the second individual; and correlating the presence of an amplified fragment to the display of the phenotype.

32. The method of claim 31 wherein providing the plurality of restriction fragments comprising an adaptor comprises:

digesting DNA of the individual with a restriction endonuclease to result in a plurality of restriction fragments, wherein each restriction fragment has two ends;

ligating a double stranded adaptor to an end of the plurality of restriction fragments.

33. The method of claim 31 further comprising repeating the producing, comparing, and correlating steps with additional individuals.

34. The method of claim 31 wherein the first individual and second individual are members of a recombinant inbred mapping population.

35. The method of claim 31 wherein at least about 70% of the miniature inverted repeat transposable elements of the miniature inverted repeat family are present in genic regions.

36. The method of claim 31 wherein the DNA is genomic DNA.

37. The method of claim 31 wherein the individual is a plant.

38. A method for generating a set of molecular markers, the method comprising:

producing a DNA fingerprint of a first individual and a DNA fingerprint of a second individual, wherein the first and the second individuals are members of different recombinant inbred lines that are members of the same mapping population, comprising;

providing a plurality of restriction fragments from each individual wherein the restriction fragments comprise an adaptor;

amplifying at least a portion of the restriction fragments with a primer pair, wherein the nucleotide sequence of one primer of the primer pair is complementary to a portion of a miniature inverted repeat transposable element that is a member of a miniature inverted repeat family, and wherein the other primer of the primer pair comprises at the 5' end a nucleotide sequence complementary to at least a portion of the adaptor; and resolving the amplified fragments to produce a DNA fingerprint of each individual; and comparing the amplified fragments of the first individual and the'second individual to detect at least one polymorphism;

repeating the producing and comparing steps with additional individuals, wherein the additional individuals are members of different recombinant inbred lines that are members of the same mapping population as the first and second individuals; and determining the linkage between the at least one polymorphism and a set of known markers.

39. The method of claim 38 wherein the set of known markers is selected from the group consisting of RFLP markers and AFLP markers.

* * * * *

UNITED STATES PATENT AND TRADEMARK OFFICE
CERTIFICATE OF CORRECTION

PATENT NO. : 6,420,117 B1
DATED : July 16, 2002
INVENTOR(S) : Wessler et al.

It is certified that error appears in the above-identified patent and that said Letters Patent is hereby corrected as shown below:

Column 21,
Line 48, please delete "Deomonstrates" and insert -- Demonstrates --.

Column 25,
Line 48, please delete "avaiable" and insert -- (available --.
Line 49, after the word "address" please insert -- www.agron.missouri.edu/) --

Column 46,
Line 67, before the word "adaptor" please insert -- the --.

Column 48,
Line 20, please delete """ after the word "the".

Signed and Sealed this

Seventh Day of January, 2003

JAMES E. ROGAN
*Director of the United States Patent and Trademark Office*